United States Patent
Geddes

(10) Patent No.: US 9,500,590 B2
(45) Date of Patent: *Nov. 22, 2016

(54) ASSAYS FOR PATHOGEN DETECTION USING MICROWAVES FOR LYSING AND ACCELERATING METAL-ENHANCED FLUORESCENCE

(75) Inventor: Chris D. Geddes, Bel-Air, MD (US)

(73) Assignee: UNIVERSITY OF MARYLAND, BALTIMORE COUNTY, Baltimore, MD (US)

( * ) Notice: Subject to any disclaimer, the term of this patent is extended or adjusted under 35 U.S.C. 154(b) by 322 days.

This patent is subject to a terminal disclaimer.

(21) Appl. No.: 13/990,828

(22) PCT Filed: Dec. 1, 2011

(86) PCT No.: PCT/US2011/062771
§ 371 (c)(1),
(2), (4) Date: Jul. 9, 2013

(87) PCT Pub. No.: WO2012/075220
PCT Pub. Date: Jun. 7, 2012

(65) Prior Publication Data
US 2014/0030700 A1 Jan. 30, 2014

Related U.S. Application Data

(63) Continuation-in-part of application No. 13/218,890, filed on Aug. 26, 2011, now Pat. No. 9,075,018, which is a continuation of application No. 12/036,402, filed on Feb. 25, 2008, now Pat. No. 8,008,067, said application No. 13/218,890 is a continuation-in-part of application No. PCT/US2007/062041, filed on Feb. 13, 2007.

(60) Provisional application No. 61/418,591, filed on Dec. 1, 2010, provisional application No. 60/902,982, filed on Feb. 23, 2007, provisional application No. 60/773,037, filed on Feb. 13, 2006.

(51) Int. Cl.
| | | |
|---|---|---|
| C12Q 1/68 | (2006.01) | |
| C07H 21/00 | (2006.01) | |
| G01N 1/34 | (2006.01) | |
| G01N 21/64 | (2006.01) | |
| C12N 1/06 | (2006.01) | |
| C12N 13/00 | (2006.01) | |
| C12Q 1/04 | (2006.01) | |

(52) U.S. Cl.
CPC ........... G01N 21/6486 (2013.01); C12N 1/066 (2013.01); C12N 13/00 (2013.01); C12Q 1/04 (2013.01); G01N 21/648 (2013.01)

(58) Field of Classification Search
CPC .......... C12Q 1/68; C07H 21/00; G01N 1/34; C12N 15/1003
See application file for complete search history.

(56) References Cited

U.S. PATENT DOCUMENTS

| | | | |
|---|---|---|---|
| 5,766,953 A | * | 6/1998 | Kennedy ............... G01V 9/007 436/25 |
| 7,095,502 B2 | | 8/2006 | Lakowicz et al. |
| 7,400,397 B2 | | 7/2008 | Lakowicz et al. |
| 7,566,783 B2 | | 7/2009 | Lakowicz |
| 7,718,804 B2 | | 5/2010 | Geddes et al. |
| 7,732,215 B2 | | 6/2010 | Geddes et al. |
| 7,776,528 B2 | | 8/2010 | Lakowicz |
| 7,939,333 B2 | | 5/2011 | Geddes et al. |
| 7,989,220 B2 | | 8/2011 | Lakowicz et al. |
| 8,008,067 B2 | | 8/2011 | Geddes et al. |
| 8,027,039 B2 | | 9/2011 | Lakowicz et al. |
| 8,034,633 B2 | | 10/2011 | Geddes |
| 8,075,956 B2 | | 12/2011 | Geddes et al. |
| 8,101,424 B2 | | 1/2012 | Geddes |
| 8,114,598 B2 | | 2/2012 | Geddes et al. |
| 8,182,878 B2 | | 5/2012 | Geddes et al. |
| 8,318,087 B2 | | 11/2012 | Geddes |
| 8,338,602 B2 | | 12/2012 | Geddes et al. |
| 8,404,450 B2 | | 3/2013 | Geddes et al. |
| 8,569,502 B2 | | 10/2013 | Geddes et al. |
| 8,618,505 B2 | | 12/2013 | Geddes |

(Continued)

FOREIGN PATENT DOCUMENTS

| | | | |
|---|---|---|---|
| WO | WO2004024191 | | 3/2004 |
| WO | WO2007/095527 | * | 8/2007 |

OTHER PUBLICATIONS

Adak, G.K. et al. (2002) Trends in indigenous foodborne disease and deaths, England and Wales: 1992 to 2000. Gut 51: 832-841.
Ali, A. et al. (2009) Multiplex PCR for differential diagnosis of emerging typhoidal pathogens directly from blood samples. Epidemiol Infect 137: 102-107.
Almeida, C. et al. (2010) Fluorescence in situ hybridization method using a peptide nucleic acid probe for identification of *Salmonella* spp. in a broad spectrum of samples. Appl Environ Microbiol 76: 4476-4485.

(Continued)

*Primary Examiner* — Ethan C Whisenant
(74) *Attorney, Agent, or Firm* — Marianne Fuierer; Moore & Van Allen, PLLC

(57) ABSTRACT

The present invention relates to an assay for the determination of a microorganism including a lysing chamber having triangular shaped metallic structures wherein the apexes of two triangles are arranged in alignment and forming a reactive zone for placement of the microorganism and lysing by microwave energy for exposing and isolating a target polynucleotide sequence. The isolated target polynucleotide sequence is introduced to an assay system for contact with polynucleotides which are complimentary to the isolated target polynucleotide sequence. Fluorophore-labeled capture polynucleotides are added for hybridizing to any bound target polynucleotide. Bound target polynucleotides are detected by metal enhanced fluorescence.

15 Claims, 13 Drawing Sheets

(56) References Cited

U.S. PATENT DOCUMENTS

| | | | |
|---|---|---|---|
| 8,679,402 B2 | 3/2014 | Geddes | |
| 8,679,855 B2 | 3/2014 | Geddes | |
| 8,722,428 B2 | 5/2014 | Geddes | |
| 8,735,175 B2 | 5/2014 | Geddes | |
| 8,759,110 B2 | 6/2014 | Geddes | |
| 9,075,018 B2* | 7/2015 | Geddes | G01N 21/76 |
| 9,170,197 B2* | 10/2015 | Geddes | C12Q 1/6816 |
| 2003/0228682 A1 | 12/2003 | Lakowicz | |
| 2006/0256331 A1 | 11/2006 | Geddes | |
| 2007/0269826 A1 | 11/2007 | Geddes | |
| 2008/0215122 A1 | 9/2008 | Geddes | |
| 2009/0022766 A1 | 1/2009 | Geddes | |
| 2009/0325199 A1 | 12/2009 | Geddes | |
| 2011/0020946 A1 | 1/2011 | Geddes | |
| 2011/0207236 A1 | 8/2011 | Geddes | |
| 2012/0021443 A1 | 1/2012 | Geddes | |
| 2012/0028270 A1 | 2/2012 | Geddes | |
| 2012/0107952 A1 | 5/2012 | Geddes | |
| 2012/0282630 A1 | 11/2012 | Geddes | |
| 2013/0115710 A1 | 5/2013 | Geddes | |
| 2013/0156938 A1 | 6/2013 | Geddes | |

OTHER PUBLICATIONS

"APHL/CDC Panel Summary Reports, Laboratory Diagnostic Testing for Chlamydia trachomatis and Neisseria gonorrhoeae, and Laboratory Diagnostic Testing for Treponema pallidum. 2009. Guidelines for the Laboratory Testing of STDs. http://www.aphl.org/aphlprograms/infectious/std/Pages/stdtestingguidelines.aspx..'".

Aslan, K. et al. (2005) Microwave-accelerated metal-enhanced fluorescence: Platform technology for ultrafast and ultrabright assays. Analytical Chemistry, vol. 77, pp. 8057-8067.

Aslan, K. et al. (2005) Annealed silver-island films for ap, plications in metal-enhanced fluorescence: interpretation in terms of radiating plasmons. J Fluoresc 15: 643-654.

Aslan, K. et al. (2006) Microwave-Accelerated Metal-Enhanced Fluorescence (MAMEF) with silver colloids in 96-well plates: Application to ultra fast and sensitive immunoassays, High Throughput Screening and drug discovery. Journal of Immunological Methods, vol. 312, pp. 137-147.

Aslan, K. et al. (2006) Microwave Accelerated and Metal Enhanced Fluorescence Myoglobin Detection on Silvered Surfaces: Potential Application to Myocardial Infarction Diagnosis, Plasmonics, vol. 1, pp. 53-59.

Aslan, K. et al. (2006) Microwave-accelerated Metal-enhanced Fluorescence (MAMEF): Application to ultra fast and sensitive clinical assays. Journal of Fluorescence, vol. 16, pp. 3-8.

Aslan, K. et al. (2007) Microwave-accelerated metal-enhanced fluorescence: an ultra-fast and sensitive DNA sensing platform. Analyst, vol. 132, pp. 1122-1129.

Aslan, K. et al. (2007) Microwave-accelerated metal-enhanced fluorescence: application to detection of genomic and exosporium anthrax DNA in <30 seconds. Analyst, vol. 132, pp. 1130-1138.

Aslan, K. et al. (2008) New tools for rapid clinical and bioagent diagnostics: microwaves and plasmonic nanostructures. Analyst 133: 1469-1480.

Aslan, K. et al. (2008) Extraction and detection of DNA from Bacillus anthracis spores and the vegetative cells within 1 min. Anal Chem 80: 4125-4132.

Aslan, K. et al. (2008) A review of an ultrafast and sensitive bioassay platform technology: Microwave-accelerated metal-enhanced fluorescence. Plasmonics 3: 89-101.

Berkley, J.A. et al. (2005) Bacteremia among children admitted to a rural hospital in Kenya. N Engl J Med 352: 39-47.

Brent, A.J. et al. (2006) Salmonella bacteremia in Kenyan children. Pediatr Infect Dis J 25: 230-236.

Centers for Disease Control and Prevention, sexually transmitted disease surveillance, 2008. Atlanta, GA: U.S. Department of Health and Human Services, CDC., 2010.

Durmaz, G. et al. (2003) Optimum detection times for bacteria and yeast species with the BACTEC 9120 aerobic blood culture system: evaluation for a 5-year period in a Turkish university hospital. J Clin Microbiol 41: 819-821.

Frankel, G. (1994) Detection of Salmonella typhi by PCR. J Clin Microbiol 32: 1415.

Gaydos, C. A. et al. (2003) J. Schachter, 'Performance of the APTIMA Combo 2 assay for the multiplex detection of Chlamydia trachomatis and Neisseria gonorrheae in female urine and endocervical swab specimens.,' J Clin Microbiol vol. 304, pp. 304-309.

Gradel, K.O. et al. (2006) Incidence and prognosis of non-typhoid Salmonella bacteraemia in Denmark: a 10-year county-based follow-up study. Eur J Clin Microbiol Infect Dis 25: 151-158.

Graham, S.M. et al. (2000) Clinical presentation of non-typhoidal Salmonella bacteraemia in Malawian children. Trans R Soc Trop Med Hyg 94: 310-314.

Graham, S.M. et al. (2000) Nontyphoidal Salmonella infections of children in tropical Africa. Pediatr Infect Dis J 19: 1189-1196.

Haque, A. et al. (2001) Utility of PCR in diagnosis of problematic cases of typhoid. Jpn J Infect Dis 54: 237-239.

Hatta, M. et al. (2007) Detection of Salmonella typhi by nested polymerase chain reaction in blood, urine, and stool samples. Am J Trop Med Hyg 76: 139-143.

Hill, P.C. et al. (2007) Bacteraemia in patients admitted to an urban hospital in West Africa. BMC Infect Dis 7: 2.

Huppert, J. et al. (2010) What's the point? How point-of-care sexually transmitted infection tests can impact infected patients., Point of Care, vol. 9, pp. 36-46.

Ikumapayi, U.N. et al. (2007) Molecular epidemiology of community-acquired invasive non-typhoidal Salmonella among children aged 2-29 months in rural Gambia and discovery of a new serovar, Salmonella enterica Dingiri. J Med Microbiol 56: 1479-1484.

Jones, T.F. et al. (2008) Salmonellosis outcomes differ substantially by serotype. J Infect Dis 198: 109-114.

Kariuki, S. et al. (2006) Characterisation of community acquired non-typhoidal Salmonella from bacteraemia and diarrhoeal infections in children admitted to hospital in Nairobi, Kenya. BMC Microbiol 6: 101.

Kennedy, M. et al. (2004) Hospitalizations and deaths due to Salmonella infections, FoodNet, 1996-1999. Clin Infect Dis 38 Suppl 3: S142-S148.

Kumar, A. et al. (2002) Detection of Salmonella typhi by polymerase chain reaction: implications in diagnosis of typhoid fever. Infect Genet Evol 2: 107-110.

Lehmann, L.E. et al. (2008) A multiplex real-time PCR assay for rapid detection and differentiation of 25 bacterial and fungal pathogens from whole blood samples. Med Microbiol Immunol 197: 313-324.

Lepage, P. et al. (1987) Community-acquired bacteraemia in African children. Lancet 1: 1458-1461.

Levy, H. et al. (2008) PCR method to identify Salmonella enterica serovars Typhi, Paratyphi A, and Paratyphi B among Salmonella isolates from the blood of patients with clinical enteric fever. J Clin Microbiol 46: 1861-1866.

Malorny, B. et al. (2008) Enumeration of Salmonella bacteria in food and feed samples by real-time PCR for quantitative microbial risk assessment. Appl Environ Microbiol 74: 1299-1304.

Mancini, N. et al. (2008) Molecular diagnosis of sepsis in neutropenic patients with haematological malignancies. J Med Microbiol 57: 601-604.

Mandomando, I. et al. (2009) Invasive non-typhoidal Salmonella in Mozambican children. Trop Med Int Health 14: 1467-1474.

Massi, M.N. et al. (2003) Rapid diagnosis of typhoid fever by PCR assay using one pair of primers from flagellin gene of Salmonella typhi. J Infect Chemother 9: 233-237.

Nga, T.V. et al. (2010) The sensitivity of real-time PCR amplification targeting invasive Salmonella serovars in biological specimens. BMC Infect Dis 10: 125.

O'Dempsey, T.J. et al. (1994) Importance of enteric bacteria as a cause of pneumonia, meningitis and septicemia among children in a rural community in The Gambia, West Africa. Pediatr Infect Dis J 13: 122-128.

(56) References Cited

OTHER PUBLICATIONS

Paolucci, M. et al. (2009) Laboratory diagnosis of late-onset sepsis in newborns by multiplex real-time PCR. J Med Microbiol 58: 533-534.

Papaevangelou, V. et al. (2004) *Salmonella* bacteraemia in a tertiary children's hospital. Scand J Infect Dis 36: 547-551.

Prakash, P. et al. (2005) Evaluation of nested PCR in diagnosis of typhoid fever. J Clin Microbiol 43: 431-432.

Pribik, R. et al. (2009) Metal-Enhanced Fluorescence (MEF): Physical characterization of silver Island Films and exploring sample geometries. Chemical Physics Letters, vol. 478, pp. 70-74.

Reisner, B.S. et al. (1999) Times to detection of bacteria and yeasts in BACTEC 9240 blood culture bottles. J Clin Microbiol 37: 2024-2026.

Sanchez-Jimenez, M.M. et al. (2004) Validation of a PCR for diagnosis of typhoid fever and salmonellosis by amplification of the *hilA* gene in clinical samples from Colombian patients. J Med Microbiol 53: 875-878.

Song, J.H. et al. (1993) Detection of *Salmonella typhi* in the blood of patients with typhoid fever by polymerase chain reaction. J Clin Microbiol 31: 1439-1443.

Tennant, S.M. et al. (2010) Identification by PCR of non-typhoidal *Salmonella enterica* serovars associated with invasive infections among febrile patients in Mali. PLoS Negl Trop Dis 4: e621.

Threlfall, E.J. et al. (1992) *Salmonella* bacteraemia in England and Wales, 1981-1990. J Clin Pathol 45: 34-36.

Van Der Pol, D. F. B. et al. (2001) Multicenter evaluation of the BDProbeTec ET system for the detection of Chalmydia trachomatis and Neisseria gonorrhoeae in urine specimens, female endocervical swabs, and male urethral swabs. J Clin Microbiol, vol. 39, pp. 1008-1016.

Vaughan, O.P.H. et al. (2006) Direct Observation of Surface-Mediated Thioacetyl Deprotection: Covalent Tethering of a Thiol-Terminated Porphyrin to the Ag(100) Surface, J. Am. Chem. Soc., vol. 128, pp. 9578-9579.

Voetsch, A.C. et al. (2004) FoodNet estimate of the burden of illness caused by nontyphoidal *Salmonella* infections in the United States. Clin Infect Dis 38 Suppl 3: S127-S134.

Vugia, D.J. et al. (2004) Invasive *Salmonella* infections in the United States, FoodNet, 1996-1999: incidence, serotype distribution, and outcome. Clin Infect Dis 38 Suppl 3: S149-S156.

Wain, J. et al. (1998) Quantitation of bacteria in blood of typhoid fever patients and relationship between counts and clinical features, transmissibility, and antibiotic resistance. J Clin Microbiol 36: 1683-1687.

Wain, J. et al. (2001) Quantitation of bacteria in bone marrow from patients with typhoid fever: relationship between counts and clinical features. J Clin Microbiol 39: 1571-1576.

Wain, J et al. (2008) The laboratory diagnosis of enteric fever. J Infect Developing Countries 2: 421-425.

Walsh, A.L. et al. (2000) Bacteremia in febrile Malawian children: clinical and microbiologic features. Pediatr Infect Dis J 19: 312-318.

Woods, D.F. et al. (2008) Rapid multiplex PCR and real-time TaqMan PCR assays for detection of *Salmonella enterica* and the highly virulent serovars Choleraesuis and Paratyphi C. J Clin Microbiol 46: 4018-4022.

Zhang, Y. et al. (2010) Development of a Microwave-Accelerated Metal-Enhanced Fluorescence 40 second, 100 cfu/mL Point of Care Assay for the Detection of *Chlamydia trachomatis*. IEEE Trans Biomed Eng.

Zhou, L. et al. (2010) A fast and highly sensitive blood culture PCR method for clinical detection of *Salmonella enterica* serovar Typhi. Ann Clin Microbiol Antimicrob 9: 14.

\* cited by examiner

GGATCCTGATAAAACATGGTAATTGCCTCGCATAACGCGGTGTGAAAATGGATTGAAGCCCGGGCGGTGG
ATTCTACTCAACTTTAGCCGATGGAGAAAGCCCCGGGATCCGGCTATTAAAAAGAAGATCTTTTTATTT
AGAGATCTGTTCTATTGTGATCTC*TTATTAGGATCGCGCCAGGC*TGTGGATAACCCGGATCCTGTAATAA
AGATCAATGCGTTGGAAAGGATCACTAGCTGTGAATGATCGGTGATCGTGGTCCGTATAAGCTGGGATCA
AAACGGGTACTTATACACAACTCAAAAA*GTGAACAACGGTTATTCTTT*GGATAACTACCGGTTGATCCAA
GCTTTCCACCAGATTTATCCACAATGGATCGCACGATCTTTACACTTATTTGAGTAAATTAATCCAGGAT
CCGAGCCAAATCTCCGCTGGATCTTCCGGAATCTCATGTTCAAGGATGTTGATCTTCAGTGTTTCCCCAA
CCTGTTTTGCGCCAGCGCCTTTCAGTTCCGCTTCTATTTTCTCAATCGCGCCGCAAAACGTGTC 3′

T in *S*. Gallinarum, *S*. Agona and *S*. Dublin

B
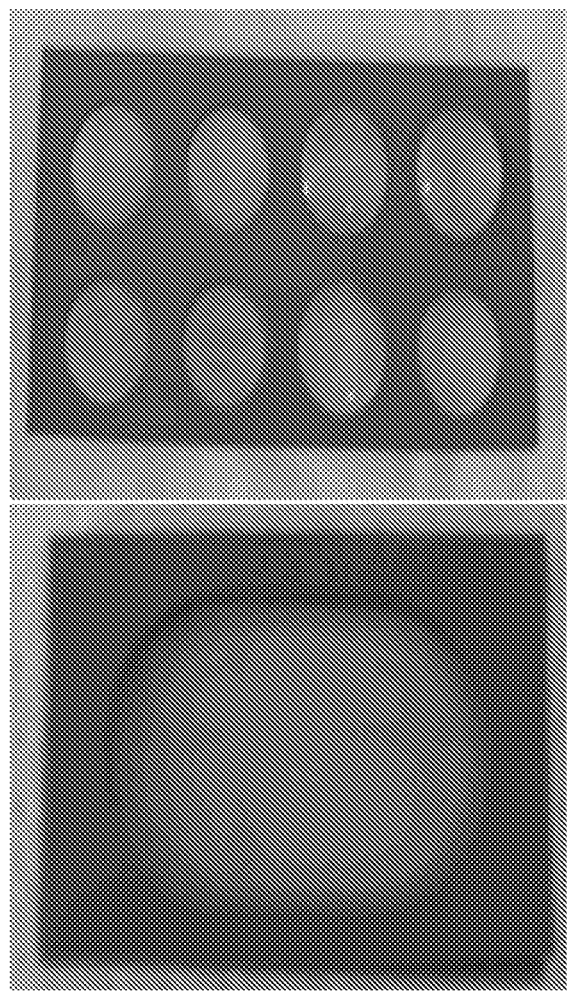
200 µl wells
2 mL well
Figure 3 Contd.

| Before lysed (cfu) | After lysed | lysed rate |
|---|---|---|
| $10^6$ | 0 | 100% |
| $10^5$ | 0 | 100% |
| $10^4$ | 0 | 100% |
| $10^3$ | 0 | 100% |
| $10^2$ | 0 | 100% |
| 10 | 0 | 100% |
| 1 | 0 | 100% |
| 0.1 | 0 | 100% |
| 0.01 | 0 | 100% |

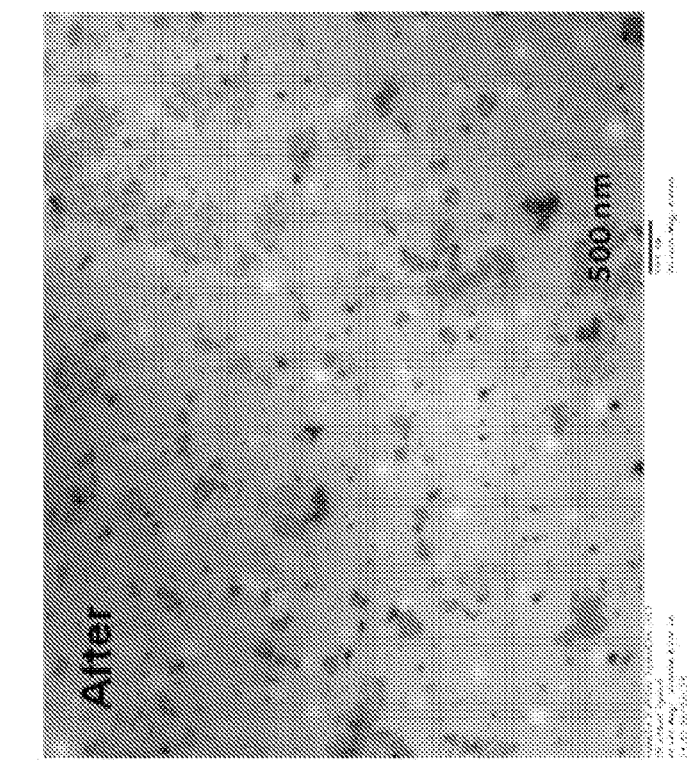
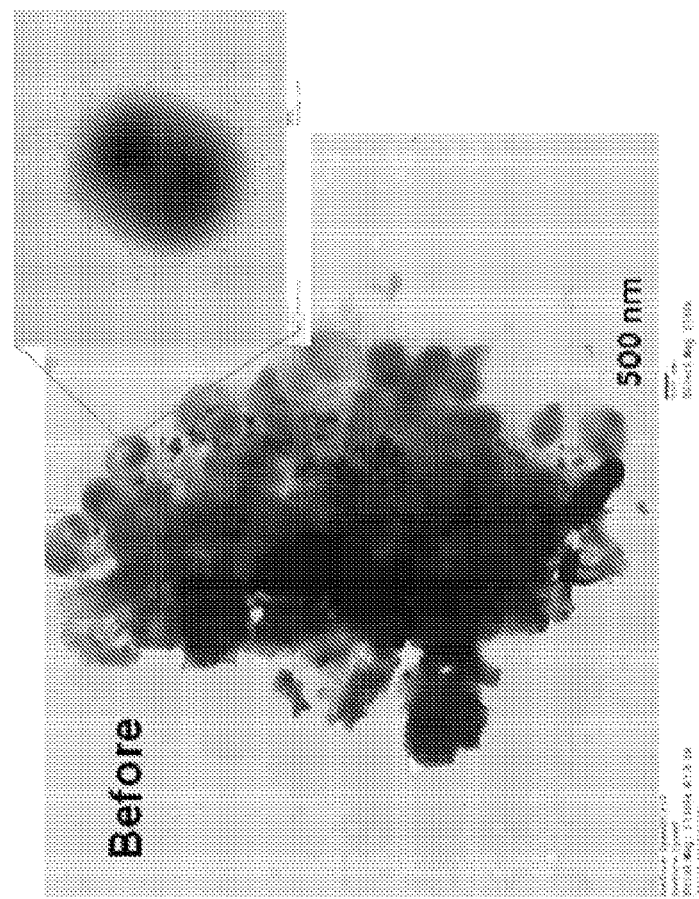
Figure 8

ASSAYS FOR PATHOGEN DETECTION USING MICROWAVES FOR LYSING AND ACCELERATING METAL-ENHANCED FLUORESCENCE

CROSS-REFERENCE TO RELATED APPLICATIONS

This application is filed under the provisions of 35 U.S.C. §371 and claims the priority of International Patent Application No. PCT/US2011/062771 filed on Dec. 1, 2011 which in turn claims priority of U.S. Provisional Application No. 61/418,591 filed on Dec. 1, 2010, the contents of which are incorporated by reference herein for all purposes and is a Continuation-in-Part of U.S. patent application Ser. No. 13/218,890 now U.S. Pat. No. 9,075,018 which in turn is a continuation of application Ser. No. 12/036,402 filed on Feb. 25, 2008 now U.S. Pat. No. 8,008,067 which is a Continuation in Part of Application No PCT/US2007/062041 filed on Feb. 13, 2007 which claims priority to Provisional Application No. 60/902,982 filed on Feb. 23, 2007 and Provisional Application No. 60/773,037 filed on Feb. 13, 2006.

BACKGROUND OF THE INVENTION

1. Field of Invention

The present invention relates generally to methods and systems for detecting a microorganism, and more particularly, to methods and systems for lysing of the cellular membrane of the microorganism and using highly sensitive microwave-accelerated metal-enhanced fluorescence (MA-MEF) technology.

2. Description of the Related Art

The ability to accurately identify biological organisms and/or biological pathogens that threaten the health of humans in real time will enable clinicians to make informed decisions about the most appropriate countermeasures.

*Salmonella*, a genus of more than 2500 serological variants (serovars), includes many organisms that can cause human disease. *Salmonella enterica* subsp. *enterica Typhi* and *S. Paratyphi* A and B cause, respectively, typhoid and paratyphoid fevers (enteric fevers), febrile illnesses characterized by infection of the gut-associated lymphoid tissue, liver, spleen, bone marrow and gall bladder and accompanied by a low level bacterium.[1] Non-typhoidal *Salmonella* (NTS) generally produce a self-limited gastroenteritis (vomiting, fever and diarrhea) in healthy hosts.[2-4] By contrast, in young infants, the elderly and immunocompromised hosts, NTS can cause severe, fatal disease in the USA [4,5] and abroad.[2, 6-12]

The most common serotypes isolated from blood in the USA are *S. Typhimurium* (24%), *S. Enteritidis* (19%) and S. Heidelberg (15%).[13] *S. Typhimurium* and *S. Enteritidis* are also the most commonly isolated NTS serovars from blood and other normally sterile sites in Europe,[14,15] United Kingdom[16] and in Africa.[9,10,17-19] *S. Typhimurium* and *S. Enteritidis* account for 80-90% of all invasive NTS in sub-Saharan Africa.[6, 9, 10, 12, 17-21]

Invasive *Salmonella* spp. is routinely detected by standard blood culture techniques. Culturing blood specimens has become much faster and easier since the advent of continuously monitoring blood culture instruments such as the BACTEC 9000 systems (Becton Dickinson, Cockeysville, Md.). However, it still takes several days for detection of *Salmonella*. For example, using the BACTEC 9240 system, of 21 *Salmonella* spp. recovered from blood culture bottles, 13 were detected on day 1, 7 on day 2 and 1 on day 6.[22] Another study using the BACTEC 9120 found that the 36 *Salmonella* spp. isolated were detected between 14.51 and 31.96 hours (median detection time of 19.48 hours).[23]

Following detection, the bacteria must still be isolated from the blood and identified by standard microbiological techniques and the serovar is ascertained by agglutination with commercial antisera (normally at a reference laboratory). Due to the time required for blood culture identification and the fact that many diagnostic labs are unable to serotype *Salmonella* spp. themselves, alternative methods of identification of *Salmonella* are being sought.[24] In particular, DNA detection tests such as PCR have been investigated. The food industry routinely uses PCR to detect *Salmonella* in food. [25, 26]

There are many reports of PCR primers designed to detect *S. Typhi* from the blood of enteric fever patients.[27-35] Furthermore, the sensitivity of PCR has often been found to be higher than that of blood culture.[29,30,32,33] However, PCR has not yet become an established method for diagnosis of typhoid fever.[24] One reason for this may be that although some reports claim high sensitivity, with detection of as few as 10 CFU/mL of blood,[34] Wain et al.'s prospective study of the concentration of *S. Typhi* in blood of typhoid fever patients showed a median value of 0.3 (range of 0.1 to 399) CFU/mL, well below current PCR-based detection limits.[36] Interestingly, in another study, Wain et al. [37] showed that 63% of the *S. Typhi* cells were located in the buffy coat layer (presumably in monocytes and polymorphonuclear leukocytes) and the mean number of bacteria per infected leukocyte was 1.3 CFU/cell. The quantitative cultures of Wain et al. corroborate the classic early study of Watson [38] who showed a median of 6 CFU/ml of *S. Typhi* in 15 patients with typhoid fever. NTS have been shown to be present at a similar concentration (M. A. Gordon, unpublished results). Detection of NTS directly from blood has not been investigated.

Another bacteria pathogen that requires a point of care testing method is *Chlamydia trachomatis* (CT) which is the most prevalent bacterial sexually transmitted infection (STIs) reported to the Centers for Disease Control and Prevention (CDC)[56]. There were 1.2 million cases of *Chlamydia* reported to the CDC in 2008. CDC estimates that STIs cost the health care system $1.5 billion annually [57]. Since these infections are most often asymptomatic, the CDC and other professional organizations recommend yearly screening for *Chlamydia* in all sexually active women ages 16-25 years of age[58]. Although there are several commercial assays available for performing nucleic acid amplifications tests (NAATs) [59-61], which are now recommended by CDC as the test of choice (APHL), they are time consuming, not convenient for use and not considered point of care tests. Currently there are no commercially available POC assays for the detection of *Chlamydia* that have rapid, high enough sensitivity and specificity to be recommended [62]. In this regard, there is a great need to develop rapid detection technologies for testing *Chlamydia* infections using point of care (POC) assays in order to expedite immediate diagnosis and treatment in both private and public health care settings.

The need for "real-time" (<60 mins) detection has lead to the development of technologies based on DNA (PCR) and protein (antibody) targets. PCR and reverse transcriptase PCR assays have been reported for detecting the pathogen anthrax in air samples. However, these advances are not considered simple or monetarily reasonable, and therefore, limit their potential as field-deployable, emerging technologies for use in ultra-sensitive pathogen detection. Thus, there is a pressing need for a sensitive and specific rapid diagnostic test to detect pathogens and preferably able to differentiate between multiple pathogenic agents, that does not suffer from the problems of the prior art and does not require any amplification steps, such as in PCR or ELISA.

SUMMARY OF THE INVENTION

The present invention provides for an ultra-fast, highly sensitive microwave-accelerated metal-enhanced fluorescence (MAMEF) technology that can be adapted so that, ultimately, it will be able to detect a pathogen within a few minutes.

The MAMEF technology couples the benefits of two technologies: 1) Metal-Enhanced Fluorescence (MEF) which increases the sensitivity of fluorescence-based bioassays[65], and 2) low power microwave heating which reduces the bioassay run time by kinetically accelerating the biological recognition events, with assay run times reduced over 1000-fold. MEF can substantially increase the sensitivity of detection. This is due to the enhancement of fluorescence emission in the near-field, by the presence of metallic nanoparticles: the excited fluorophores partially transfer their energy to the silver nanoparticles where it is amplified and the emission from the fluorophore-silver "system" becomes greater than the emission from fluorophores alone. It is this unique combination of enhanced fluorescence emission coupled with a significantly reduced bioassay run times that makes MAMEF a very powerful technology for fluorescence-based ultra-fast and sensitive bioassays.

The present invention uses MAMEF for the detection of target DNA released from a lysed microorganism such as bacteria, viruses, yeast, algae, or any microorganism that with an isolatable DNA. The DNA is released from the microorganism by lysing with the application of a low-power microwave based approach utilizing centimeter-sized metallic disjointed "bow-tie" structures to focus the microwaves into a lysing volume. A 5 s to 60 s focused microwave burst, preferably about 10 s to 20 s, is sufficient to induce morphological changes in a microorganism. Such detection of DNA was accomplished by combining the focused microwave lysis technology and MAMEF platform technology of the present invention.

In one aspect, the present invention relates to a method for detecting a pathogen using a single-copy number detection method without the need for any amplification steps that can also be applied to the detection of plague, smallpox, tularemia, botulism (botulinum toxin) anthrax, *Chlamydia, salmonella* or any other organism or pathogen where the DNA sequence is known or easily determined.

In another aspect, the present invention provides a method for detecting a pathogenic microorganism in a sample, the method comprising:
a) providing a system comprising:
  i) a first surface substrate comprising immobilized triangular shaped metallic structures, wherein the triangular shaped metallic structures are in a patterned shape of a bow-tie wherein the apexes of two triangles are arranged in alignment and forming a reactive zone between the apexes;
  ii) a second surface substrate comprising immobilized metallic islands or colloids, wherein the metallic islands or colloids has attached thereto an immobilized capture DNA sequence probe complementary to a known DNA sequence of the pathogenic microorganism;
  iii) a free capture DNA sequence probe complementary to a known DNA sequence of the pathogenic microorganism, wherein the free capture DNA sequence probe has attached thereto an excitable light emitting molecule, such as a fluorophore;
  iv) a source of electromagnetic energy that can provide energy in the microwave energy range and energy to irradiate and excite the excitable light emitting molecule, optionally the source can be a single source or two sources; and
  v) a measuring device to measure electromagnetic emissions;
b) contacting the sample with the first surface substrate and positioning the pathogenic microorganism in the reactive zone;
c) exposing the reactive zone to microwave energy in an amount sufficient to lyse cellular membranes of the pathogenic microorganism to form lysed pathogenic microorganisms;
d) removing the lysed microorganisms from the first substrate and isolating the DNA from the lysed pathogenic microorganism;
e) contacting the isolated DNA with the immobilized capture DNA sequence probe on the second substrate, wherein the isolated DNA of the pathogenic microorganism binds to the immobilized capture DNA sequence probe;
f) introducing the free capture DNA sequence probe for contact with any bound DNA of pathogenic microorganism, wherein binding of the free capture DNA sequence probe to the DNA of pathogenic microorganism causes the excitable light emitting molecule to be positioned a sufficient distance from the immobilized metallic islands or colloids to enhance emission levels when excited by an irradiating source;
g) exposing the binding reactions of steps (e) and (f) to microwave energy in an amount sufficient to increase the reaction rate; and
g) identifying the pathogenic microorganism by luminescence emission by irradiating the system with the electromagnetic energy to excite the excitable light emitting molecule.

The light emitting molecule includes but is not limited to fluorophores, luminophores, bioluminescent species and chemiluminescent species.

The first surface substrate comprises metallic material deposited on the sample plate surface including silver, gold, copper, zinc, indium, rhodium, aluminum, or platinum wherein the metallic material is formed into a patterned shape. Preferably, the patterned shape includes geometric shapes having at least one apex, such as, a triangle, square, rectangle, trapezoid, polygon, parabola, elliptical, a sector of a circle, oblong and/or combinations thereof, wherein the numerous apexes are adjacent to each other, thereby creating a reactive zone therebetween. The reactive zone therebetween may further be prepared for placement of the immobilized capture molecule complementary to a detector molecule, chemicals for reacting with other chemicals, or biomolecules for reacting with other biomolecules. The reactive zone may have a diameter or distance between the adjacent and/or opposing apexes ranging from about 0.01 mm to 10 mm, and more preferably from about 1 mm to 3 mm. Further, the reactive zone can be positioned on assay system with multiple wells wherein the reactive zone is within the wells and exposure to microwave energy causes lysing of included microorganism and/or enhances the reactions therein.

The first and second surface substrate may be fabricated of a polymeric material, glass, paper, nitrocellulose, combinations thereof or any material that provides sufficient stability for placement of the metallic material.

The apex area/reactive zone is exposed to microwave energy in an amount to cause lysing of cellular material; increase the reaction rate in biological interactions; increase intensity of emissions from the chemiluminescence reaction, fluorescence, phosphorescence or luminescence tags in sensing technologies; and enhance electric fields by focusing electromagnetic fields in the reactive zone.

In still a further aspect, the above-described method further comprises a metal colloid attached to the free capture DNA sequence probe and positioned for sandwiching the fluorophore between the metal colloid and immobilized metal particles on the surface substrate.

Another aspect of the present invention relates to an assay system for determining a target pathogen comprising:
 a surface substrate comprising immobilized triangular shaped metallic structures positioned in a patterned shape of a bow-tie wherein the apexes of two triangles are arranged in alignment and forming a reactive zone between the apexes;
 a captured DNA probe complementary to a known DNA sequence of the target pathogen immobilized on the triangular shaped metallic structures;
 a free DNA probe complementary to the known DNA of the target pathogen, wherein the free DNA probe has attached thereto an excitable light emitting molecule, wherein binding of the immobilized and free DNA probe to the known DNA sequence of the target pathogen causes the light emitting molecule to be positioned from about 5 nm to about 200 nm, more preferably from about 5 nm to 40 nm from the immobilized triangular shaped metallic structures to enhance light and/or electromagnetic emission.

Notably, the pathogenic microorganism is placed in the reactive zone and exposed to microwave energy in an amount sufficient to lyse cellular membranes of the pathogenic microorganism to form lysed pathogenic microorganisms. The DNA from the lysed pathogenic microorganism is contacted with the immobilized capture DNA sequence probe on the metallic structures, wherein the isolated DNA of the pathogenic microorganism binds to the immobilized capture DNA sequence probe; and then the free capture DNA sequence probe with the fluorophore to provide a visual signal when excited by an irradiating source.

A further aspect of the present invention, relates to a kit for detecting a target pathogen in a sample, the kit comprising:
 a container comprising a layer of triangular shaped immobilized metal particles deposited on a surface substrate, wherein the triangular metal particles are in a patterned shape of a bow-tie wherein the apexes of two triangles are arranged in alignment and forming a reactive zone;
 a captured biomolecular probe is immobilized on the metal particles and wherein the captured biomolecular probe has an affinity for a biomolecule of the target pathogen of interest; and
 a free biomolecular probe having an affinity for a biomolecule of the target pathogen, wherein the free biomolecular probe has attached thereto a fluorophore and wherein binding of the biomolecule of the target pathogen to both the immobilized and free biomolecular probe causes the fluorophore to be positioned a sufficient distance from the immobilized metal particles to enhance fluorescence emission, wherein the immobilized and free biomolecular probe can be in the same or different containers.

The assay kit described above, provides for lysing of a target pathogenic microorganism and subsequent determination of DNA in the same container or surface without the need for isolating the DNA from the cellular biomass before moving on to the detection of the target DNA.

Other aspects and advantages of the invention will be more fully apparent from the ensuing disclosure and appended claims.

BRIEF DESCRIPTION OF THE DRAWINGS

FIG. 2 shows location of oriC primer binding sites and *Salmonella* MAMEF target DNA (SEQ ID NO: 4) in the *S. Typhimurium* LT2 genome. Bold, segment of DNA targeted by *Salmonella* MAMEF assay; underlined, primer binding sites of oriC primers described by Woods et al.[54]; and italicized, primer binding sites of oriC primers described by Widjojoatmodjo et al.[55]

FIG. 8 shows transmission electron micrograph images of *Chlamydia* A) before B) after lysing.

DETAILED DESCRIPTION OF THE PRESENT INVENTION

Figure 1:
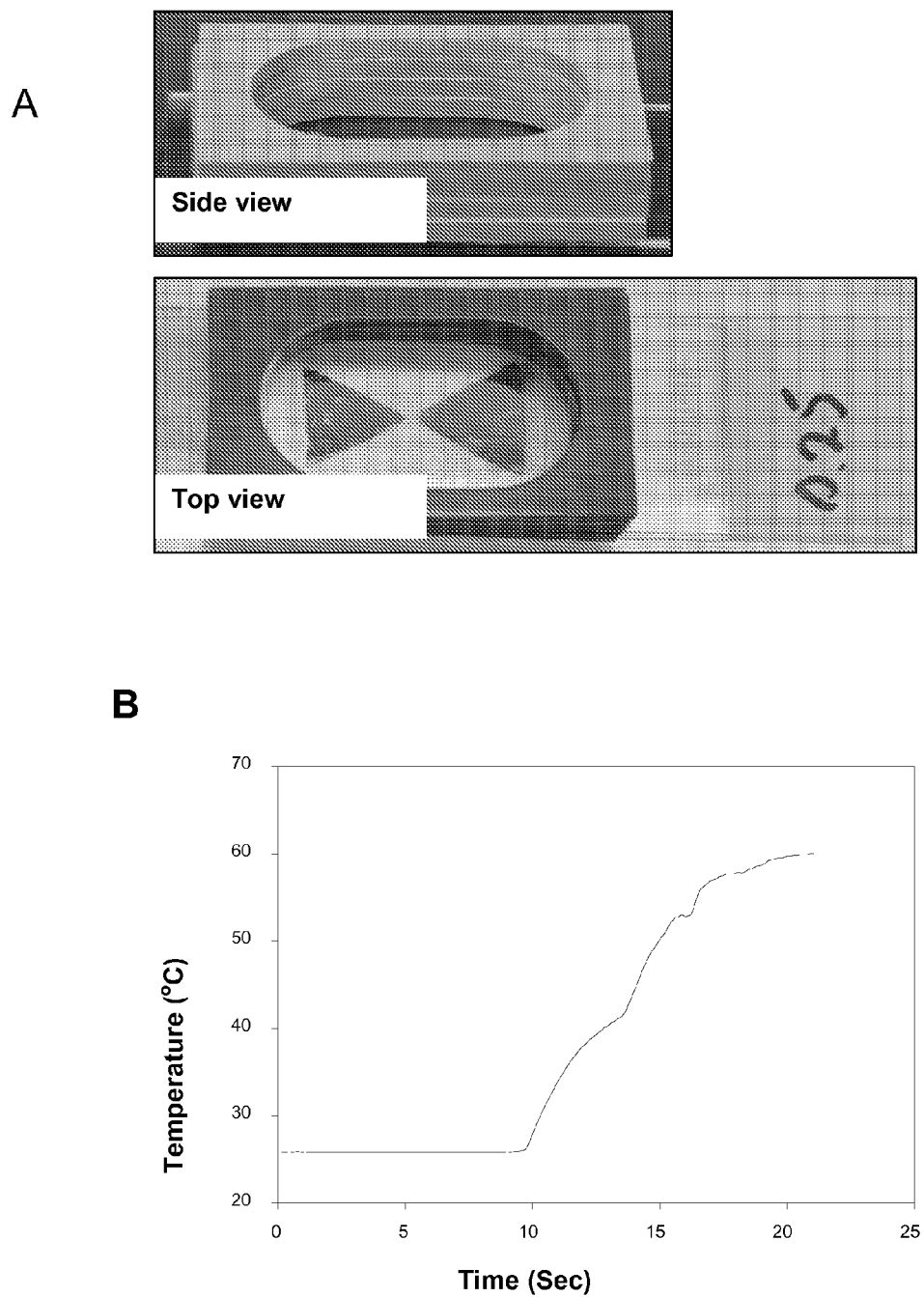
FIG. 1A shows gold lysing triangles with 'bow-tie' configuration; B Temperature at the apex of the gold bow-tie triangles over time, C Lysis of biological relevant concentrations of *S. Enteritidis* R11 ΔguaBA (pGEN206). 2 CFU/mL to $1.3 \times 10^4$ CFU/mL were lysed using gold lysing triangles and heated for 13 s on high power in a GE microwave Model No. JE2160BF01, D Agarose gel of DNA released from lysed *S. Enteritidis* R11 ΔguaBA (pGEN206). An overnight culture of bacteria ($1.9 \times 10^{10}$ CFU/mL) was lysed using gold lysing triangles and microwave radiation. Lane 1, 1 kb Plus DNA ladder (Invitrogen); 2, lysed bacteria; 3, unlysed bacteria, E Transmission electron micrographs of lysed and unlysed *S. Enteritidis* R11 ΔguaBA (pGEN206). Bar=500 nm.
Figure 1:
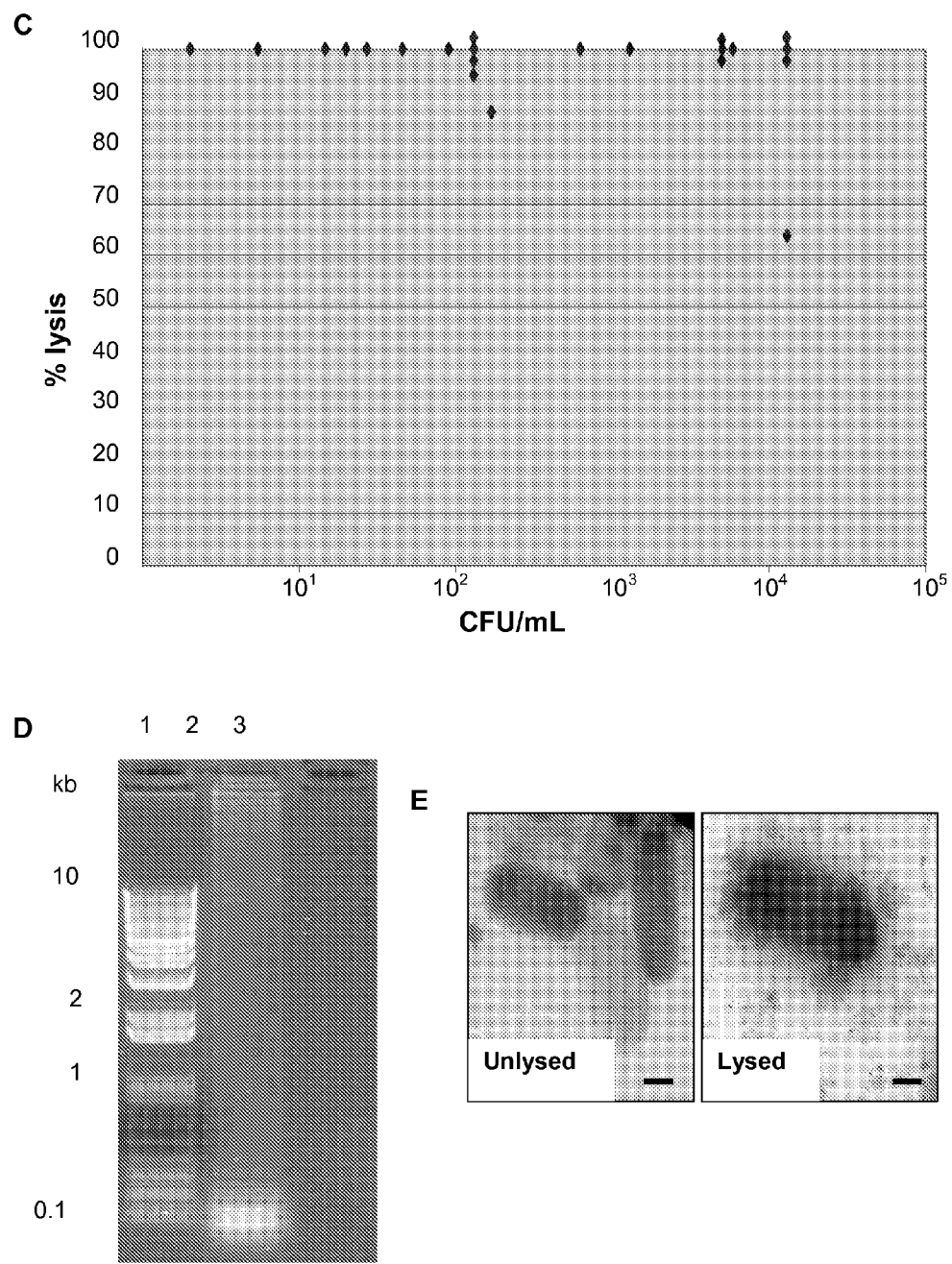

Before the present invention is disclosed and described, it is to be understood that this invention is not limited to the particular process steps and materials disclosed herein as such process steps and materials may vary somewhat. It is also to be understood that the terminology used herein is used for the purpose of describing particular embodiments only and is not intended to be limiting since the scope of the present invention will be limited only by the appended claims and equivalents thereof.

It must be noted that, as used in this specification and the appended claims, the singular forms "a," "an," and "the" include plural references unless the content clearly dictates otherwise.

The term "biomolecule" means any carbon based molecule occurring in nature or a derivative of such a molecule. The biomolecule can be in active or inactive form. "Active form" means the biomolecule is in a form that can perform a biological function. "Inactive form" means the biomolecule must be processed either naturally or synthetically before the biomolecule can perform a biological function. Exemplary biomolecules include nucleic acids, aromatic carbon ring structures, NADH, FAD, amino acids, carbohydrates, steroids, flavins, proteins, DNA, RNA, oligonucleotides, peptide nucleic acids, fatty acids, sugar groups such as glucose etc., vitamins, cofactors, purines, pyrimidines, formycin, lipids, phytochrome, phytofluor, peptides, lipids, antibodies and phycobiliproptein.

Fluorophore," and "fluorescence label," used interchangeably herein, means any substance that emits electromagnetic energy such as light at a certain wavelength (emission wavelength) when the substance is illuminated by radiation of a different wavelength (excitation wavelength) and is intended to encompass a chemical or biochemical molecule or fragments thereof that is capable of interacting or reacting specifically with an analyte of interest in a sample to provide one or more optical signals. Additionally fluorophore includes both extrinsic and intrinsic fluorophores. Extrinsic fluorophore refer to fluorophores bound to another substance. Intrinsic fluorophores refer to substances that are fluorophores themselves. Exemplary fluorophores include but are not limited to those listed in the Molecular Probes Catalogue which is incorporated by reference herein.

Representative fluorophores include but are not limited to Alexa Fluor® 350, Dansyl Chloride (DNS-Cl), 5-(iodoacetamida)fluoroscein (5-IAF); fluoroscein 5-isothiocyanate (FITC), tetramethylrhodamine 5-(and 6-)isothiocyanate (TRITC), 6-acryloyl-2-dimethylaminonaphthalene (acrylodan), 7-nitrobenzo-2-oxa-1,3,-diazol-4-yl chloride (NBD-Cl), ethidium bromide, Lucifer Yellow, 5-carboxyrhodamine 6G hydrochloride, Lissamine rhodamine B sulfonyl chloride, Texas Red™ sulfonyl chloride, BODIPY™, naphthalamine sulfonic acids including but not limited to 1-anilinonaphthalene-8-sulfonic acid (ANS) and 6-(p-toluidinyl) naphthalen-e-2-sulfonic acid (TNS), Anthroyl fatty acid, DPH, Parinaric acid, TMA-DPH, Fluorenyl fatty acid, Fluorescein-phosphatidylethanolamine, Texas red-phosphatidylethanolamine, Pyrenyl-phophatidylcholine, Fluorenyl-phosphotidylcholine, Merocyanine 540, 1-(3-sulfonatopropyl)-4-[-.beta.-[2[(di-n-butylamino)-6 naphthyl]vinyl]pyridinium betaine (Naphtyl Styryl), 3,3' dipropylthiadicarbocyanine (diS-$C_3$-(5)), 4-(p-dipentyl aminostyryl)-1-methylpyridinium (di-5-ASP), Cy-3 Iodo Acetamide, Cy-5-N-Hydroxysuccinimide, Cy-7-Isothiocyanate, rhodamine 800, IR-125, Thiazole Orange, Azure B, Nile Blue, Al Phthalocyanine, Oxaxine 1, 4', 6-diamidino-2-phenylindole (DAPI), Hoechst 33342, TOTO, Acridine Orange, Ethidium Homodimer, N(ethoxycarbonylmethyl)-6-methoxyquinolinium (MQAE), Fura-2, Calcium Green, Carboxy SNARF-6, BAPTA, coumarin, phytofluors, Coronene, and metal-ligand complexes.

Representative intrinsic fluorophores include but are not limited to organic compounds having aromatic ring structures including but not limited to NADH, FAD, tyrosine, tryptophan, purines, pyrimidines, lipids, fatty acids, nucleic acids, nucleotides, nucleosides, amino acids, proteins, peptides, DNA, RNA, sugars, and vitamins. Additional suitable fluorophores include enzyme-cofactors; lanthanide, green fluorescent protein, yellow fluorescent protein, red fluorescent protein, or mutants and derivates thereof.

Fluorophores with high radiative rates have high quantum yields and short lifetimes. Increasing the quantum yield requires decreasing the non-radiative rates $k_{nr}$, which is often only accomplished when using a low solution temperature or a fluorophore bound in a more rigid environment. The natural lifetime of a fluorophore, $\tau_n$, is the inverse of the radiative decay rate or the lifetime which would be observed if their quantum yields were unity. This value is determined by the oscillator strength (extinction coefficient) of the electronic transition. Hence, for almost all examples currently employed in fluorescence spectroscopy, the radiative decay rate is essentially constant. The modification and control of the radiative rate have also been referred as Radiative Decay Engineering (RDE), or "lightening rod" fluorescence enhancement effect. For example, enhanced intrinsic DNA fluorescence above metallic particles has recently been observed, which is typically not readily observable because of DNA's very low quantum yield of less than $10^{-4}$. The second favorable "lightening rod" effect also increases the fluorescence intensity by locally enhanced excitation. In this case, emission of fluorophores can be substantially enhanced irrespective of their quantum yields.

The reduction in lifetime of a fluorophore near a metal is due to an interaction between the fluorophore and metal particle, which enhances the radiative decay rate (quantum yield increase) or depending on distance, $d^{-3}$, causes quenching. It should be noted that lifetimes of fluorophores with high quantum yields (0.5) would decrease substantially more than the lifetimes of those with low quantum yields (0.1 and 0.01). A shorter excited-state lifetime also allows less photochemical reactions, which subsequently results in an increased fluorophore photostability. Notably, the use of low quantum yield fluorophores would lead to much larger fluorescence enhancements (i.e. $1/Q_0$) and could significantly reduce unwanted background emission from fluorophores distal from the silvered assay.

Fluorophore photostability is a primary concern in many applications of fluorescence. This is particularly true in single molecule spectroscopy. A shorter lifetime also allows for a larger photon flux. The maximum number of photons that are emitted each second by a fluorophore is roughly limited by the lifetime of its excited state. For example, a 10 ns lifetime can yield about $10^8$ photons per second per molecule, but in practice, only $10^3$ photons can be readily observed. The small number of observed photons is typically due to both photo-destruction and isotropic emission. If a metal surface decreases the lifetime, one can obtain more photons per second per molecule by appropriately increasing the incident intensity.

On the other hand, the metal-enhanced fluorescence provides enhanced intensity, while simultaneously shortening the lifetime. That is, it may be possible to decrease the excitation intensity, yet still see a significant increase in the emission intensity and photostability.

The emission enhancement may be observed at distances according to the type of fluorophore to be detected and the type, shape of the metal material, noting a difference between a film and a metallic island or colloid. For example, emission enhancement may be observed when a fluorophore is positioned from about 5 nm to about 200 nm from the metal surfaces. Preferable distances are about 5 nm to about 30 nm, and more preferably, 5 nm to about 20 nm to metal surfaces. At this scale, there are few phenomena that provide opportunities for new levels of sensing, manipulation, and control. However, the present invention leads to dramatically enhanced performance, sensitivity, and reliability with dramatically decreased size, weight, and therefore cost.

Attaching of the fluorophore to a probe may be achieved by any of the techniques familiar to those skilled in the art. For example, the fluorophore may be covalently attached to the bimolecular probe by methods disclosed in U.S. Pat. Nos. 5,194,300 (Cheung) and 4,774,189 (Schwartz).

In another embodiment, the assay system of the present invention provides for detecting and separating at least two target pathogen by choosing fluorophores such that they possess substantially different emission spectra, preferably having emission maxima separated by greater than 10 nm, more preferably having emission maxima separated by greater than 25 nm, even more preferably separated by greater than 50 nm. When differentiation between the two fluorophores is accomplished by visual inspection, the two dyes preferably have emission wavelengths of perceptibly different colors to enhance visual discrimination. When it is desirable to differentiate between the two fluorophores using instrumental methods, a variety of filters and diffraction gratings allow the respective emission maxima to be independently detected.

In addition to the use of a fluorophore, the present invention envisions the use of any chemiluminescent species in the present invention that provides for a chemical reaction which produces a detectable reaction (observed emission) wherein the excited state responsible for the observed emission including, but not limited to the following excitation mechanisms:

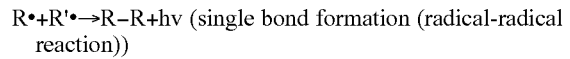
R•+R'•→R–R+hv (single bond formation (radical-radical reaction))

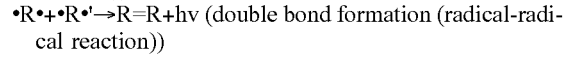
•R•+•R•'→R=R+hv (double bond formation (radical-radical reaction))

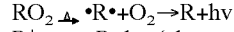
$RO_2 \xrightarrow{\Delta}$ •R•+$O_2$→R+hv

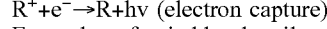
$R^+ + e^- \rightarrow R + hv$ (electron capture)

Examples of suitable chemiluminescence detector molecules include but without limitation, peroxidase, bacterial luciferase, firefly luciferase, functionalized iron-porphyrin derivatives, luminal, isoluminol, acridinium esters, sulfonamide and others. A recent chemiluminescent label includes xanthine oxidase with hypoxanthine as substrate. The triggering agent contains perborate, a Fe-EDTA complex and luminol. Choice of the particular chemiluminescence labels depends upon several factors which include the cost of preparing labeled members, the method to be used for covalent coupling to the detector molecule, and the size of the detector molecules and/or chemiluminescence label. Correspondingly, the choice of chemiluminescence triggering agent will depend upon the particular chemiluminescence label being used.

Chemiluminescent reactions have been intensely studied and are well documented in the literature. For example, peroxidase is well suited for attachment to the detector molecule for use as a chemiluminescence. The triggering agent effective for inducing light emission in the first reaction would then comprise hydrogen peroxide and luminol. Other triggering agents which could also be used to induce a light response in the presence of peroxidase include isobutyraldehyde and oxygen.

Procedures for labeling detector molecules, such as antibodies or antigens with peroxidase are known in the art. For example, to prepare peroxidase-labeled antibodies or antigens, peroxidase and antigens or antibodies are each reacted with N-succinimidyl 3-(2-pyridyldithio)proprionate (hereinafter SPDP) separately. SPDP-labeled peroxidase, or SPDP-labeled antigen or antibody is then reacted with dithiothreitol to produce thiol-labeled peroxidase, or thiol-labeled antigen or antibody. The thiol derivative is then allowed to couple with the SPDP-labeled antigen or antibody, or SPDP-labeled peroxidase.

The present invention provides enhanced emissions using metallic structures of elliptical, spherical, triangular, rod-like forms or any geometric form. In exemplary cases, the elliptical islands have aspect ratios of 3/2, and the spherical colloids have diameters of 20-60 nm. Using known coating techniques, the placement of metallic structures could be controlled precisely, as close as 50 nm apart.

Further, the metallic structures can be fabricated in other geometric shapes besides the triangular, such as square, oblong, elliptical, rectangle, or any shape that provides at least one apex area of the metallic surface. It is envisioned that the apex area includes not only pointed regions but regions with rounded edges such as found in an oblong or elliptical shape. The apex areas are preferably arranged so that one apex area is opposite from another apex area and aligned to cause the reactive zone to be positioned therebetween. The distances between the apex areas may range from 0.01 mm to 10 mm, more preferably from 1 mm to about 3 mm and depending on the size of the required reactive zone.

The present invention further comprises a detection device for detecting emissions including, but not limited to visual inspection, digital (CCD) cameras, video cameras, photographic film, or the use of current instrumentation such as laser scanning devices, fluorometers, luminometers, photodiodes, quantum counters, plate readers, epifluorescence microscopes, fluorescence correlation spectroscopy, scanning microscopes, confocal microscopes, capillary electrophoresis detectors, or other light detector capable of detecting the presence, location, intensity, excitation and emission spectra, fluorescence polarization, fluorescence lifetime, and other physical properties of the fluorescent signal.

Excitation light sources can include arc lamps and lasers, natural sunlight, laser diodes and light emitting diode source, and both single and multiple photon excitation sources. In another embodiment, use of a Ti-sapphire laser, Laser Diode (LD) or Light Emitting Diode Sources (LEDs) may be used with the RNA assay of the present invention. For example, using 2-photon excitation at 700-1000 nm and also using short pulse width (<50 pi), high repetition rate (1-80 MHz), laser diode and LED (1 ns, 1-10 MHz) sources. The enhanced sensitivity of the assay using 2-photon excitation, as compared to 1-photon, can be shown by using series dilution with RNA, initially with the Ti-Sapphire system, and later with LEDs and LDs. If a fluorophore absorbs two photons simultaneously, it will absorb enough energy to be raised to an excited state. The fluorophore will then emit a single photon with a wavelength that depends on the fluorophore used and typically in the visible spectra. The use of the Ti-sapphire laser with infrared light has an added benefit, that being, longer wavelengths are scattered less, which is a benefit to high-resolution imaging. Importantly, there is reduced background signal level gained by using 2-photon excitation as compared to 1-photon excitation by utilizing localized excitation near by metallic particles.

In the present invention, the application of low level microwave heating of the sample may be used to speed up any chemical/biochemical kinetics within the system. Notably, low level microwaves do not destroy or denature proteins, DNA, or RNA, but instead heat the sample sufficiently to provide for accelerated kinetics such as binding or hybridization. In addition, the microwaves are not scattered by the metallic structures, which is contrary to most metal objects, such as that recognized by placing a spoon in a microwave oven.

Microwaves (about 0.3 to about 300 GHz) lie between the infrared and radiofrequency electromagnetic radiations. Importantly, molecules absorb microwave radiation through dipole rotations and hence are heated, where as non-polar molecules do not absorb due to lower dielectric constants are thus not heated. The polar molecules align themselves with the external applied field. In the conventional microwave oven cavity employed in this work, the radiation frequency (2450 MHz) changes sign $2.45 \times 10^9$ times per second. Heating occurs due to the tortional effect as the polar molecules rotate back and forth, continually realigning with the changing field, the molecular rotations being slower than the changing electric field.

In the present invention, microwave radiation may be provided by an electromagnetic source having a frequency in a range between 0.3 and 10 GHz and a power level in a range between about 10 mwatts and 1000 watts. Any source, known to one skilled in the art may be used, such as a laser that emits light, wherein light is used in its broad sense, meaning electromagnetic radiation which propagates through space and includes not only visible light, but also infrared, ultraviolet and microwave radiation. Thus, a single instrument placed above the surface of the assay can be used to generate the microwave energy for not only the lysing process but also to provide energy to excite fluorescing molecules. The energy can be emitted from a fiber continuously or intermittently, as desired, to maintain the metallic particles at a predetermined temperature such that it is capable of increasing the speed of chemical reactions within the assay system. The microwave radiation may be emitted continuously or intermittently (pulsed), as desired. In the alternative, microwave energy can be supplied through a hollow wave guide for conveying microwave energy from a suitable magnetron.

Clearly, the level of microwave energy is sufficiently high to cause lysing of cell tissue during the lysing process, with a range of power levels between 300 watts to 1000 watts and then preferably adjusted to a lower energy level for the detection assay, that being between 30 mwatts to about 200 watts to cause an increase in the kinetics of the hybridization reaction without causing damage to any biological materials in the assay system.

Bacterial DNA may be isolated using various DNA isolation methods known in the art. A kit suitable for isolating DNA is the Roche High Pure PCR Template Preparation Kit. DNA concentration is estimated by measuring the absorbance of a solution at 260 nm. An $A_{260}$ value of 1 is equivalent to a DNA concentration of 50 µg/ml for double stranded DNA and 20 µg/ml for single-stranded DNA. The purity of a sample is assessed by calculating the 260/280 nm absorbance ratio. This is approximately a ratio greater than 1.5 for protein-free DNA samples.

Oligonucleotide sequences should be examined to ensure that the nucleotide sequence does not contain self-complementary stretches that could potentially form stem loops. Complementarities between oligonucleotide pairs is also avoided as this can lead to formation of primer-dimer artifacts. Binding of the oligomer to other regions of the template DNA is avoided by prior comparison of the DNA nucleotide sequence of the template DNA to be amplified for local high percentage match to the primer, using the PRIMER EXPRESS software package from Perkin Elmer ABI. The step of washing the assay surface after target capture will remove any non-hybridized complimentary labeled capture stands if the background fluorescence signal levels from the bulk solution are high.

The assays of the present invention may include a single substrate or a first and second substrate with transference of products from the first to the second substrate after the lysing process. The single substrate may comprise multiple triangular metallic structures with apexes forming a reactive zone between the apexes which may be used in both the lysing and detection processes. Alternatively the first substrate includes the metallic triangles and the second surface comprises silver colloids or islands wherein the first substrate is used in the lysing process and the second substrate used in the assay for detecting the DNA of a target pathogen.

Attached to the metallic triangular structures (if a single substrate is used), or silver colloids/islands are polynucleotides which are complimentary to a target polynucleotide sequence. These capture polynucleotide sequences are attached at either the 5' or 3' end. The assay is performed by adding the target polynucleotide sequence to the assay surface and allowed to hybridize with the capture polynucleotides. Fluorophore-labeled capture polynucleotides are added and hybridize to the target polynucleotide. Unbound target polynucleotide and labeled capture sequence may be removed by washing, but washing is not required. Bound target polynucleotide is detected by metal enhanced fluorescence. The target polynucleotide sequence and capture sequence are preferably single stranded but may be double stranded and may be either deoxyribonucleic acid or ribonucleic acid.

Many conditions suitable for hybridizing polynucleotides are known in the art. High stringency conditions or high stringency hybridization conditions are where polynucleotides are hybridized under the following conditions: 6×SSPE, 5×Denhardt's reagent, 50% formamide, 42° C., 0.5% SDS, 100 µg/ml sonicated denatured calf thymus or salmon sperm DNA. Medium stringency conditions or medium stringency hybridization conditions are where polynucleotides are hybridized under the following conditions: 6×SSPE, 5×Denhardt's reagent, 42° C., 0.5% SDS, 100 µg/ml sonicated denatured calf thymus or salmon sperm DNA. Low stringency conditions or low stringency hybridization conditions are where polynucleotides are hybridized under the following conditions: 6×SSPE, 5×Denhardt's reagent, 30° C., 0.5% SDS, 100 µg/ml sonicated denatured calf thymus or salmon sperm DNA. The formulae for the buffers used for hybridizations are: 20×SSPE: 3.6 M NaCl, 0.2 M phosphate, pH 7.0, 20 mM EDTA. 50×Denhardt's reagent: 5 g FICOLL Type 400, 5 g polyvinylpyrrolidone, 5 g bovine serum albumin and water to 500 ml.

It is recognized in the art of nucleotide hybridization that high, medium and low stringency hybridizations can be performed under a variety of different conditions. The provided conditions for performing nucleotide hybridizations are illustrative of the specific hybridizations for high, medium and low stringency conditions. These hybridization conditions are not intended to limit the disclosed method as one of ordinary skill in the art would recognize that the method of the instant invention is not dependent upon the disclosed hybridization conditions but can be achieved using many other different hybridization conditions.

Additionally, several different attached capture polynucleotide sequences may be used, as well as different fluorophore-labeled capture polynucleotide sequences to allow detection of more than one target polynucleotide sequence. Fluorophore-labeled capture polynucleotides of different sequences may be labeled with different fluorophores to allow identification of the different target sequences that may be present in a sample. The fluorophore-labeled capture polynucleotides may also comprise a silver colloid to further enhance fluorescence emission.

The capture immobilized DNA probe may be any length of nucleotides any preferably of a sufficient length of nucleotides to allow interaction of a bound fluorophore with the metallized surface of the substrate. The sequence may be from about 5 to about 300 nucleotides in length.

EXAMPLES

Methods and Material
Bacterial Strains, Blood and Genomic DNA

An attenuated *Salmonella Enteritidis* strain R11 ΔguaBA carrying plasmid pGEN206 was used to optimize microwave lysis and the MAMEF assay. This mutant is unable to synthesize guanine and is highly attenuated (unpublished results). The parent strain, *S. Enteritidis* R11, was isolated from the blood of a child in Mali.[11] Plasmid pGEN 206, which carries gfpUV, was used to monitor efficient lysis of bacteria by fluorescence microscopy. Other *Salmonella* strains tested included *S. Typhi* (2 strains), *S. Paratyphi* A (2 strains), *S. Paratyphi* B (2 strains), *S. Paratyphi* C (1 strain), *S. Typhimurium* (2 strains), *S. Enteritidis* (2 strains), S. Dublin (2 strains), *S. Choleraesuis* sensu stricto (1 strain), *S. Choleraesuis* var. *kunzendorf* (1 strain) and *S. Newport* (1 strain) that came from *Salmonella* collections at the CVD or the *Salmonella* Reference Laboratory at the Centers for Disease Control and Prevention (Atlanta, Ga.). Non-*Salmonella* strains used to determine specificity include *Escherichia coli* (2 strains), *Pseudomonas aeruginosa* (1 strain), *Klebsiella pneumoniae* (1 strain) and *Streptococcus pneumoniae* (1 strain each of serotypes 6b, 14, 19F and 23) and *Haemophilus influenzae* B (2 strains). All of the non-Salmonella strains were from various collections at the CVD. *Salmonella* spp., *E. coli*, *P. aeruginosa* and *K. pneumoniae* were grown in an animal product-free (APF) LB Lennox medium (APF-LB; Athena Environmental Sciences, Baltimore, Md.) at 37° C. Media was supplemented with guanine (0.001% w/v) and 50 µg/ml carbenicillin for growth of R11 ΔguaBA (pGEN206). *S. penumoniae* was grown on Columbia agar containing 5% Sheep Blood (BD, Franklin Lakes, N.J.) or in Brain Heart Infusion (BHI) broth at 37° C. with 5% $CO_2$. *H. influenzae* was grown on BHI containing 10 µg/ml nicotinamide adenine dinucleotide (NAD) and 10 µg/ml hemin anaerobically using the AnaeroPack System (Mitsubishi Gas Chemical Co., Tokyo, Japan). Whole human blood containing sodium heparin as an anticoagulant was purchased from Innovative Research (Novi, Mich.). Genomic DNA from *Acinetobacter baumanii* isolates 10 and 11 were obtained from BEI Resources (Manassas, Va.).

DNA Methods

Genomic DNA was isolated using the WIZARD SV Genomic DNA Purification system (Promega, Madison, Wis.) as per the manufacturer's instructions. DNA was visualized by agarose gel electrophoresis and staining with ethidium bromide. The concentration of DNA was determined either by a spectrophotometer or by estimating the concentration from an agarose gel. DNA released from lysed bacteria was visualized by agarose gel electrophoresis following concentration by ethanol precipitation. Briefly, 450 µl of lysed bacteria was concentrated by ethanol precipitation. The DNA pellet was resuspended in 20 µl TE and the entire volume was electrophoresed on a 0.9% agarose gel.

Anchor and Fluorescent Probes

Probes specific for the oriC locus of *Salmonella* spp. were designed using the oriC sequence from *S. Typhimurium* LT2 (GenBank accession no. AE006468). Anchor probe (5' GTTTTTCAACCTGTTTTGCGCC 3' (SEQ ID NO: 1)), fluorescent probe (5' CTTTCAGTTCCGCTTCTAT 3' (SEQ ID NO: 2)) and a synthetic target oligonucleotide (5' ATA-GAAGCGGAACTGAAAGGCGCTGGCGCAAAACAG-GTG 3' (SEQ ID NO:3)) were purchased from Sigma-Aldrich (St. Louis, Mo.). 16 nucleotides of the anchor probe bind to the oriC target. The remaining nucleotides consist of a guanine to which a thiol group is added and 5 T's for flexibility of the probe following binding to the glass slide. The fluorescent probe possesses a TAMRA dye attached to the first nucleotide at the 5' end.

Deposition of Gold Triangle on Glass Substrates to Lyse *Salmonella*.

Glass microwave slides were covered with a mask (12.5 mm in size with a 1 mm gap between two bowties), leaving a triangle bowtie region exposed. Equilateral gold triangles of 12.5 mm were subsequently deposited onto glass microscope slides through the mask using a BOC Edwards 306 vacuum deposition with vacuum $3.0 \times 10^{-6}$ Torr, with a deposition rate of ~1 A/s. Two layers of self-adhesive silicon isolators (D 2.5 mm) were placed on top of the Au bow-tie region to create a sample well, directly over the BowTie apexes.

Lysis by Microwave Radiation

Bacteria were lysed using gold bow-tie deposits on a glass slide and heating in a GE microwave Model No. JE2160BF01, kW:1.65 (M/W), for 13 seconds on maximum power, that being between 900 and 1000 watts. 2 mL bacterial suspensions were placed into wells formed by laying 4 rubber wells on top of each other. The chambers were sterilized by rinsing with 70% ethanol and air-drying. Overnight cultures of bacteria were diluted to the required concentration in APF-LB and lysed. Viable counts of unlysed samples were performed by spread-plating up to 200 µl of bacterial suspension on agar plates or by using the pour plate method (5 mL of the bacterial suspension was added to 20 ml of molten agar and poured into a petri dish). Viable counts of lysed samples were performed by spread plating 100-200 µl on APF-LB and incubating the remaining suspension at 37° C. overnight. A sample was considered to be fully lysed if the broth showed no turbidity.

Transmission Electron Microscopy.

TEM images were taken using an Electron Microscope Tecnai T12 microscope. Samples were drop cast onto Formvar carbon films on copper grids (400 mesh) by placing a droplet of a 10-μL aqueous sample solution on a grid. The grid was dried in air for 24 h.

Formation of Silver Island Films (SiFs) on Glass Substrates.

SiFs were prepared as previously published.[45] In a typical SiFs preparation, a solution of silver nitrate (0.5 g in 60 ml of deionized water) was put in a clean 100-mL glass beaker. 200 μL of freshly prepared 5% (w/v) sodium hydroxide solution and 2 ml of ammonium hydroxide were added to a continuously stirred silver nitrate solution at room temperature. Subsequently, the solution was cooled to 5° C. by placing the beaker in an ice bath, followed by soaking the Silane-Prep™ glass slides in the solution and adding a fresh solution of D-glucose (0.72 g in 15 ml of water). The temperature of the mixture was then allowed to warm to 40° C. As the color of the mixture turned from yellow green to yellowish brown, the slides were removed from the mixture, washed with water, and sonicated for 1 min at room temperature.

Preparation of MAMEF Assay Platform for Ultra Fast Detection of *Salmonella* DNA.

SiFs-deposited glass slides were coated with self-adhesive silicon isolators, containing (2.0 mm/32 mm/19 mm D/L/W) oval wells prior to the assay fabrication and subsequent fluorescence experiments. 1 μM of thiolated anchor probe was incubated overnight at 4° C. on the surface of SiFs-deposited glass slides in 1×TE Buffer. The thiolated anchor probe was covalently linked to SiFs via well-established self-assembled monolayer chemistry.

MAMEF-Based *Salmonella* DNA Assays

The MAMEF-based DNA capture assay was performed by the incubation of 1 mL lysed *Salmonella* mixed with 1 mL TAMRA-labeled fluorescent probe on the SiFs with anchor probe immobilized on, for 30 seconds in a microwave cavity (a 0.7 cu ft, GE Compact Microwave Model: JES735BF, max power 700 W). The power setting of the microwave cavity was set to 2 which corresponded to 140 W over the entire cavity. In all the experiments performed with low power microwaves, using SiFs surface there was no evidence of sample drying.

Fluorescence Spectroscopy

All fluorescence assay measurements were performed by collecting the emission intensity through a notch filter (532 nm), using a 532 nm diode laser and a Fiber Optic Spectrometer (HD2000) from Ocean Optics, Inc.

Lysis of *Salmonella*

A variety of configurations of gold deposited on glass slides was tested and it was found that the gold 'bow-tie' configuration was the best in terms of its ability to effectively lyse *Salmonella* when heated in a microwave (FIG. 1A).

Since sapphire transmits infrared radiation, it is an ideal substrate for thermal imaging experiments. A slide coated with gold triangles and containing water in the sample well was covered by a sapphire plate. Using this sapphire and metal sandwich configuration, the average temperature increase of the water in proximity to the metal was determined. The optical configuration consisted of a microwave cavity with a 1 inch diameter opening at the base, a gold mirror, and a thermal imaging camera (Silver 420 M; Electrophysics Corp, Fairfield, N.J., USA) that was equipped with a lens that provided a resolution of approximately 300 μm. The clear sapphire plate of the sandwich geometry was fixed to the base of the microwave cavity opening. A gold mirror was positioned such that the image of the opening was reflected onto the thermal camera. Thermal imaging data was recorded at 100 frames/second before, during and after the application of microwave pulses. FIG. 1B shows that the temperature of liquid at the point where the two triangles apex is raised during microwave heating.

Overnight cultures of *S. Enteritidis* R11 ΔguaBA (pGEN206) were diluted to biologically relevant concentrations (up to $10^4$ CFU/mL) in APF-LB and 2 mL was lysed by microwave radiation. As can be seen in FIG. 1C, 2 CFU/mL to $1.3 \times 10^4$ CFU/mL can be efficiently lysed (98%±8% lysis; mean±standard deviation) using gold lysing triangles and heating in a microwave. FIG. 1D shows that DNA released from an overnight culture ($1.9 \times 10^{10}$ CFU/mL) of *S. Enteritidis* R11 ΔguaBA (pGEN206), that had been lysed using gold lysing triangles and a microwave, is fragmented into a range of sizes with most of the fragments around 100 bp. FIG. 1E shows electron micrographs of lysed and unlysed bacteria. The unlysed sample shows bacteria with distinct edges and a clear background. The lysed sample shows bacteria with blurred edges that are surrounded by clumps of lysed debris.

Detection of a Synthetic oriC Oligonucleotide by MAMEF

Figure 3:
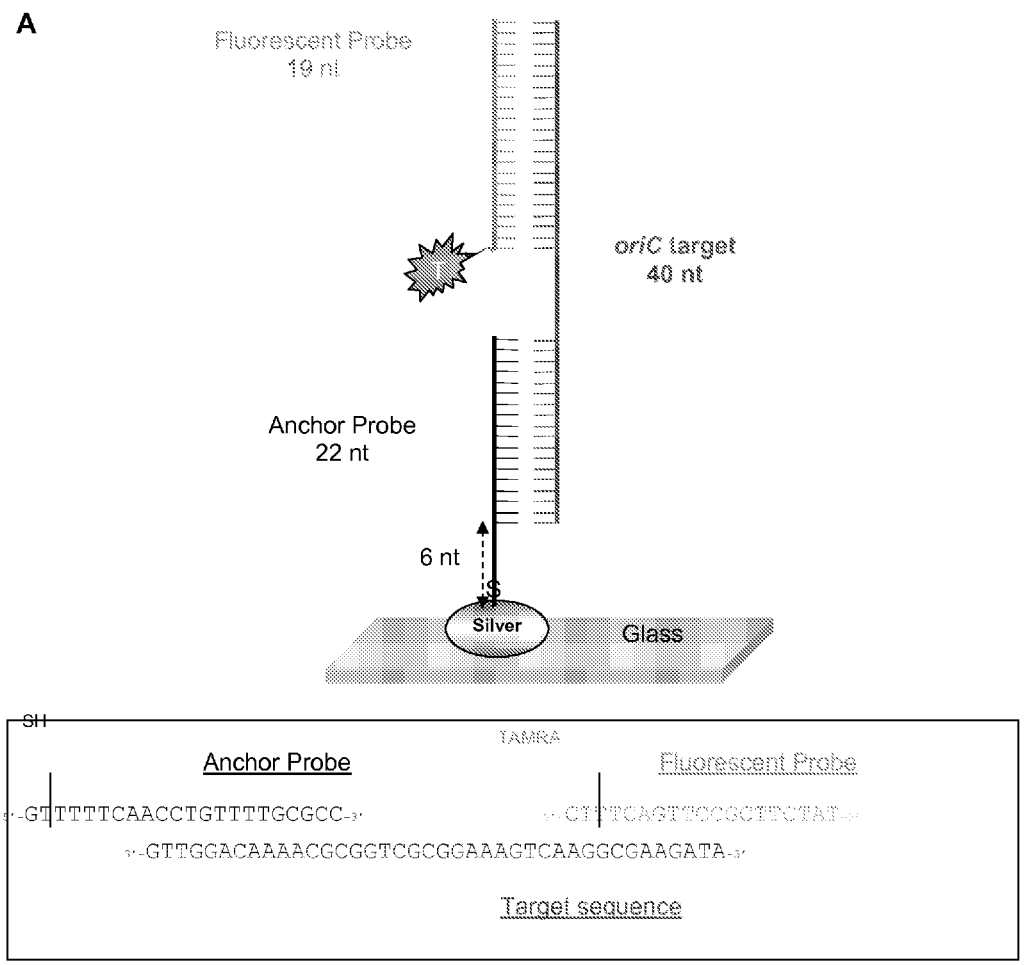
FIG. 3 show a schematic representation of anchor (SEQ ID NO; 1) and fluorescent (SEQ ID NO: 2) probes binding to *Salmonella* oriC target DNA (SEQ ID NO: 3).
Figure 4:
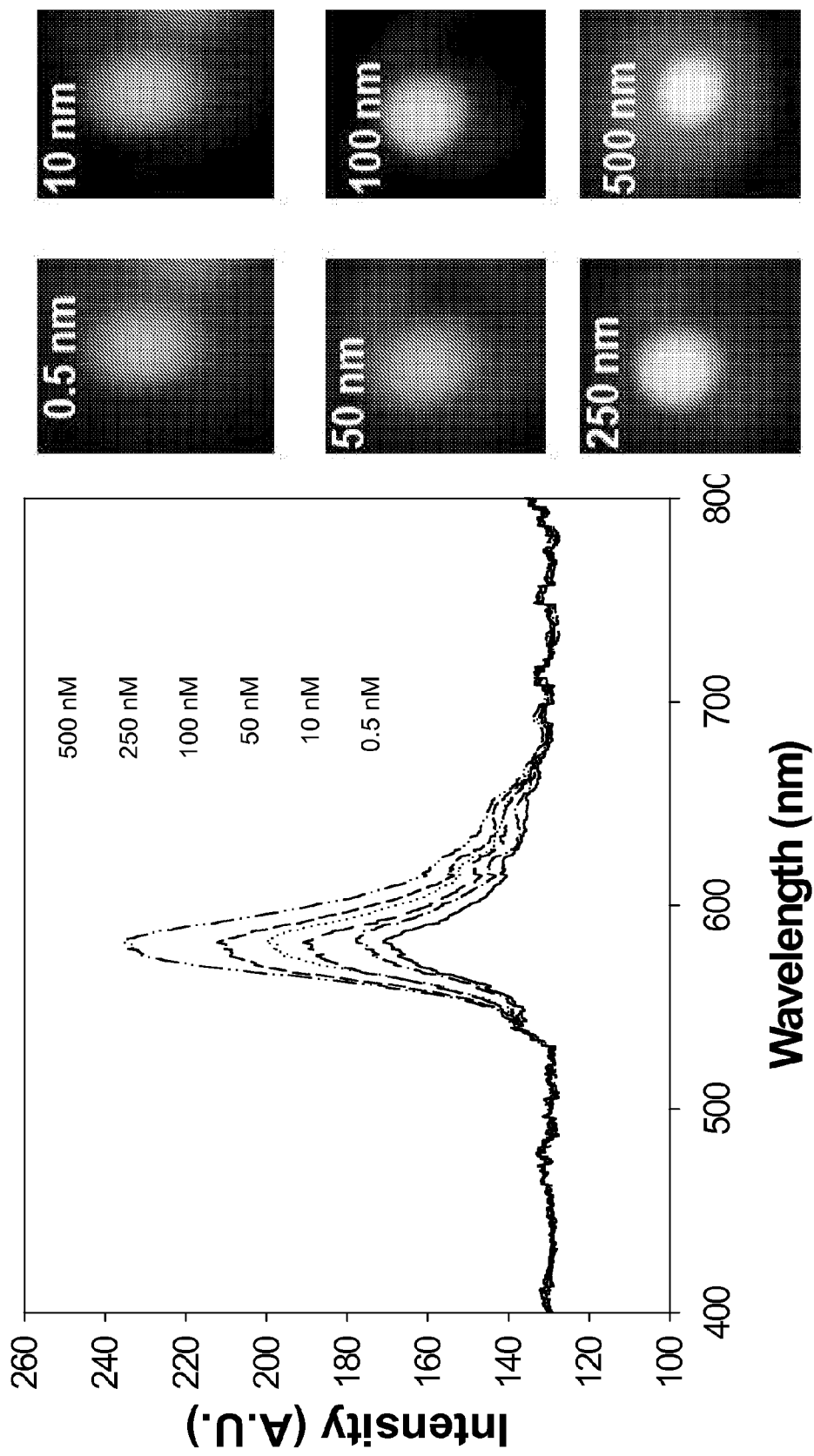
FIG. 4 shows detection of various concentrations of a synthetic oriC oligonucleotide by MAMEF. Excitation=532 nm, Emission=575 nm.

Primers were used that were found to be successful to detect oriC of *Salmonella* in several PCRs.[11,46] This region was used as a target for the *Salmonella* MAMEF assay. FIG. 2 shows the primer binding sites in *S. Typhimurium* LT2 (GenBank Accession No. AE006468) of primers used to detect oriC in several PCRs and the location of the segment of DNA that our fluorescent and anchor probes target. FIG. 3 shows a schematic diagram of the anchor and fluorescent probes binding to the target DNA. The target DNA is conserved in all serovars of *Salmonella enterica* subsp. *enterica* except for *S. Agona*, *S. Gallinarum* and *S. Dublin* (FIG. 2). The anchor and fluorescent probes were designed so that they can detect all *Salmonella enterica* subsp. *enterica* serovars including *S. Agona*, *S. Gallinarum* and *S. Dublin*. Initially, the probes were used to test the ability of the probes to detect a synthetic oligonucleotide target. As can be seen in FIG. 4, the target DNA was detected in a concentration-dependent manner as a function of the series dilution. As the concentration of the target DNA increased, so did the fluorescence signal.

Detection of DNA Released from Lysed *Salmonella*

Figure 5:
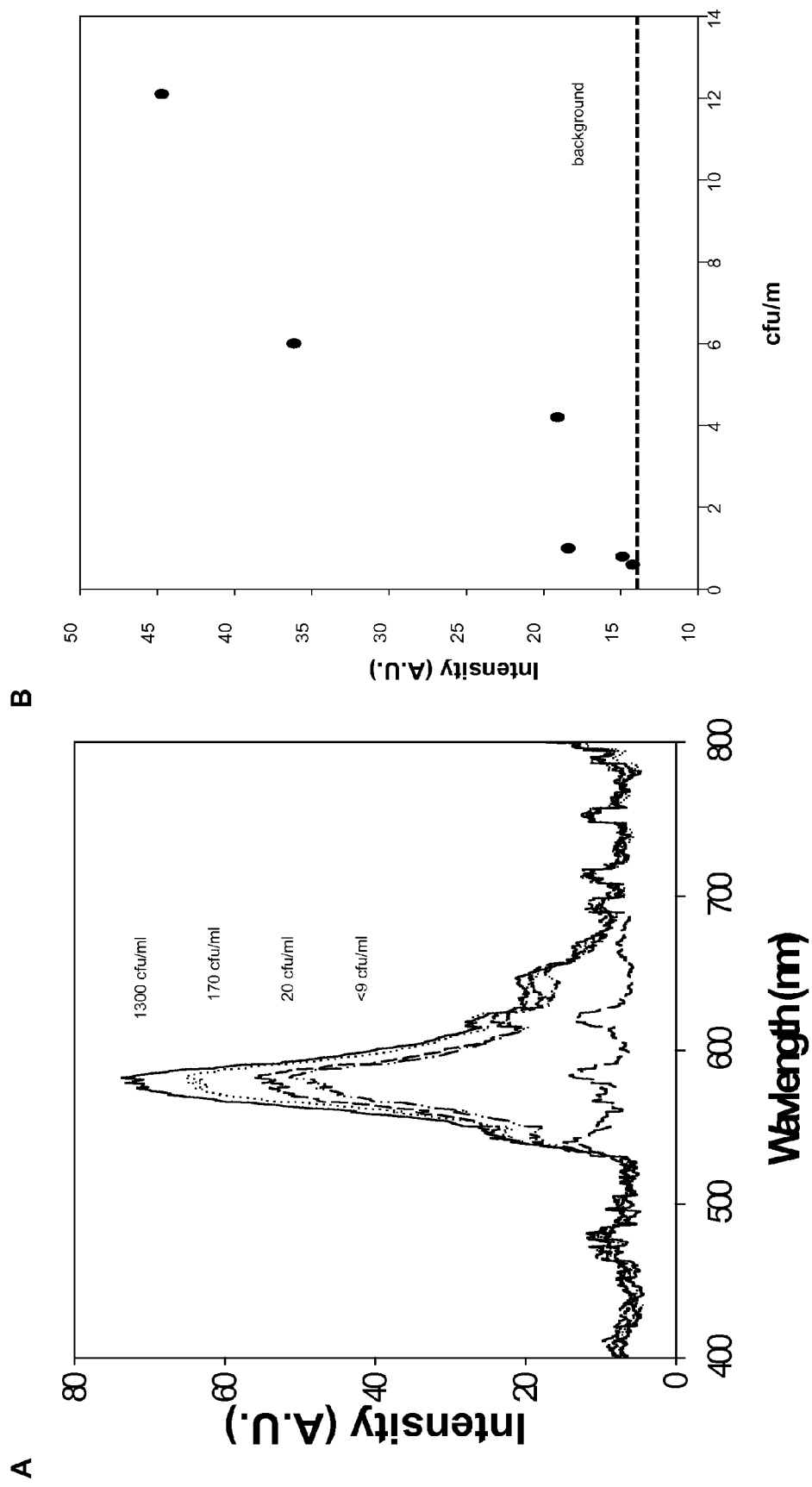
FIG. 5 shows detection of DNA released from microwave-lysed *S. Enteritidis* R11 ΔguaBA (pGEN206) suspended in bacteriological media. Two concentration curves were tested: A) 10-fold serial dilutions of a $10^3$ CFU/mL suspension and B) 2-fold serial dilutions of a 12 CFU/mL suspension.

Once lysis and detection were optimized, the two methods were performed sequentially and detected DNA using MAMEF from *Salmonella* that had been lysed by microwave radiation. Overnight cultures of *S. Enteritidis* R11 ΔguaBA (pGEN206) were diluted to biologically relevant concentrations (up to $10^3$ CFU/mL) in APF-LB and 2 mL was lysed by microwave radiation. 1 mL of the lysed bacteria was tested by MAMEF. Two concentration curves were tested. The first consisted of 10-fold serial dilutions of a $10^3$ CFU/mL suspension. The second consisted of 2-fold serial dilutions of a 12 CFU/mL suspension. Each dilution was lysed separately. Once again, the intensity of the fluorescence signal was concentration dependent (FIG. 5A). Interestingly, detection as low as 1 CFU/ml (FIG. 5B) was possible.

Specificity of the *Salmonella* MAMEF Assay

To determine whether the assay is specific in terms of its ability to detect just *Salmonella* DNA, DNA from a variety of *Salmonella* serovars and other bacteria commonly isolated from blood was tested. Sixteen *Salmonella* strains of various serovars were suspended in APF-LB media at $10^3$-$10^4$ CFU/ml and 2 ml was lysed using gold bow-tie triangles heating in a microwave. Every strain was lysed (93%±16%, mean±standard deviation). 1 mL of the lysed sample was then detected by MAMEF. A fluorescent signal was observed for every strain tested (Table 1). 2 mL of $10^4$ CFU/mL suspensions of E. coli, P. aeruginosa and K. pneumoniae were lysed by microwave lysis and 1 mL was tested by MAMEF. As can be seen in Table 1, no fluorescence signal was observed.

TABLE 1

Detection of Salmonella and non-Salmonella strains that are commonly found in blood.

| Species/serovar | Number of strains tested | Method of DNA extraction | Detection |
| --- | --- | --- | --- |
| Salmonella enterica subsp. enterica serovars | | | |
| Typhi | 2 | Microwave lysis | + |
| Paratyphi A | 2 | Microwave lysis | + |
| Paratyphi B | 2 | Microwave lysis | + |
| Paratyphi C | 1 | Microwave lysis | + |
| Typhimurium | 2 | Microwave lysis | + |
| Enteritidis | 2 | Microwave lysis | + |
| Dublin | 2 | Microwave lysis | + |
| Choleraesuis (sensu stricto) | 1 | Microwave lysis | + |
| Choleraesuis var. Kunzendorf | 1 | Microwave lysis | + |
| Newport | 1 | Microwave lysis | + |
| Non-Salmonella | | | |
| E. coli | 2 | Microwave lysis and genomic DNA isolation | – |
| P. aeruginosa | 1 | Microwave lysis and genomic DNA isolation | – |
| K. pneumoniae | 1 | Microwave lysis and genomic DNA isolation | – |
| S. pneumoniae | 4 | Genomic DNA isolation | – |
| H. influenzae | 2 | Genomic DNA isolation | – |
| A. baumannii | 2 | Genomic DNA isolation | – |

Also tested was genomic DNA (diluted to 100 pg/mL) from these 3 species as well as DNA from S. pneumoniae, H. influenzae and A. baumanii in the 100 µl assay format and did not observe any detection.

Detection of Salmonella DNA in Blood

Figure 6:
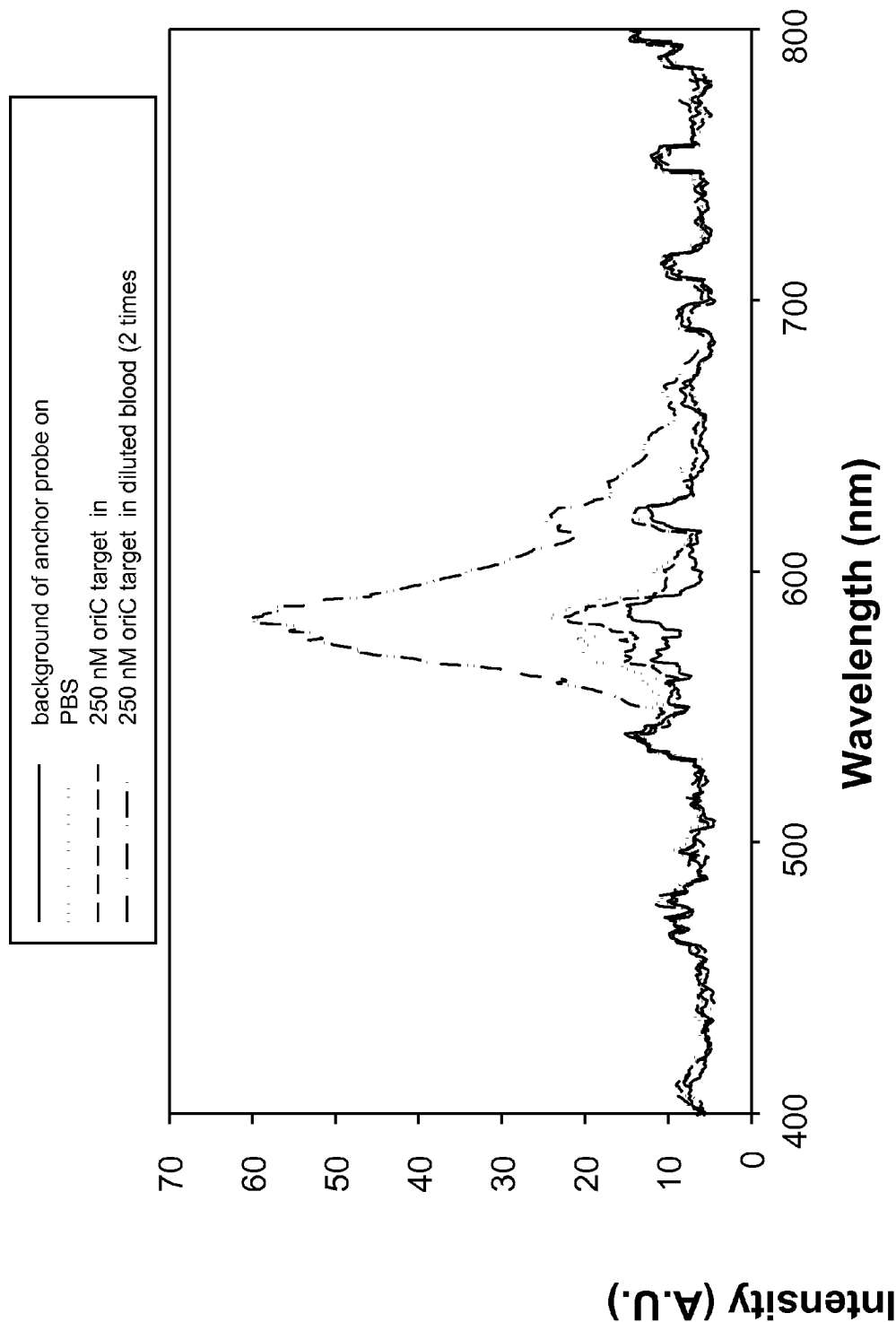
FIG. 6 shows detection of a synthetic oriC oligonucleotide suspended in whole human blood or in diluted human blood by MAMEF.

Detecting Salmonella directly from blood is more difficult and a preliminary experiment was performed using blood spiked with the synthetic oriC oligonucleotide and no fluorescence was observed (FIG. 6). However, when the spiked blood sample was diluted with an equal volume of PBS, the synthetic oriC target was readily detected by MAMEF.

Discussion

The present invention provides a MAMEF-based Salmonella assay that can lyse and detect 1 CFU suspended in 1 ml media in 30 seconds. This level of speed and detection limit greatly surpasses all currently available assays. For example, Nga et al. [47] have recently described a multiplex real-time PCR assay that targets S. Typhi and S. Paratyphi A. When the Nga investigators performed their assay on DNA extracted from blood and bone marrow samples, they found that the assay was highly specific (100% specificity) but only showed 53.9% sensitivity on all biological samples. In particular, the sensitivity of the assay on blood samples was low with only 42% sensitivity for S. Typhi and 39% sensitivity for S. Paratyphi A. This poor sensitivity is most likely due to the poor detection limit of the assay. The Nga authors prepared serial dilutions of S. Typhi in blood and observed detection limits of 250 CFU/ml for their real-time assay and 25 CFU/ml for detection by blood culture. The final PCR amplifications were performed on an equivalent volume of only 75 µl of whole blood whereas 6 ml of whole blood was tested by blood culture. Simply due to the nature of the DNA extraction and PCR procedure, the sample volume that can be tested is much lower than that of blood culture. Considering that Wain et al. [36] have shown the median concentration of S. Typhi in blood to be 0.3 CFU/ml, it is not surprising that the real-time PCR assay showed such poor sensitivity. The Wain authors concede that identification of invasive Salmonella by PCR is not a practical approach.

In another recent study, Zhou and Pollard [48] overcame low sensitivity due to small sample volumes by including a 3 hour incubation step in tryptone soya broth containing 2.4% ox bile prior to detection of S. Typhi by PCR. They were able to achieve a detection limit of 0.75 CFU per ml of blood. However, the entire protocol still takes almost 8 hours to complete. A fluorescence in situ hybridization (FISH) method for the detection of Salmonella spp. using a novel peptide nucleic acid (PNA) probe has also recently been reported.[49] The assay has 100% sensitivity and 100% specificity and can detect 1 CFU per 10 ml of blood but only after an overnight enrichment step.

One molecular assay that does not require an enrichment step is the Lightcycler SeptiFast Test MGRADE kit (Roche Diagnostics, Germany) which is a commercial real-time PCR assay. This kit detects and identifies the 25 most common pathogens known to cause bloodstream infections directly from whole blood in <6 hours.[50] In serial experiments performed on EDTA-blood samples spiked with different concentrations of bacterial and fungal reference organisms, hit rates of 70-100% were achieved for 23 out of 25 organisms at 30 CFU/ml and for only 15 out of 25 organisms at 3 CFU/ml. These results suggest that the assay may not be as sensitive as blood culture which has a theoretical sensitivity of 1 CFU. However, two studies suggest that the Lightcycler SeptiFast is more sensitive than blood culture as it was able to detect target DNA in several samples which were negative by blood culture.[51,52] Disadvantages of this method are that it includes a sample preparation step that requires the use of a centrifuge and the time taken to detection.

The key points of the present MAMEF technology of the present invention is that it makes it ideal for detection of pathogens in blood include: 1) rapid and highly sensitive, 2) the technology has been multiplexed, so that in one sample well, presently three DNA or protein targets can be identified within 20 seconds, 3) the cost per well is estimated to be less than other methods, 4) detection of well fluorescence can be accomplished by a variety of standard inexpensive sample well-reader technologies 5) assay platform is completely wash-less, in that no washing steps are needed to remove excess fluorescent probe or labeled DNA/antibody, 6) chambers are disposable to minimize cross-contamination, and 7) no centrifugation steps are required. These attributes make it possible for the assay to ultimately be developed into a point-of-care device that can be used by people with minimal training.

The novel aspects of the present invention include: 1) development of a sensitive and specific MAMEF-based Salmonella assay, 2) detection in 1 ml sample volumes which is greater than previously tested (and which provides the proof-in-principle that large volumes can be tested by MAMEF), 3) lysing and detecting Salmonella without any centrifugation or washing steps, and 4) detection in blood is possible.

Further studies were conducted with *Chlamydia trachomatis* using the initial deposition of Gold Triangles on glass substrates to lyse *Chlamydia trachomatis*. Glass microwave slides were covered with a mask (12.5 mm in size and 1 mm gap size) leaving a triangle bowtie region exposed. Equilateral gold triangles of 12.5 mm and 100 nm thickness were deposited onto the glass microscope slides using a BOC Edwards 306 vacuum deposition unit, with a deposition rate of 0.1 nm/s. Two layers of self-adhesive silicon isolators (D=2.5 mm) were placed on top of the bow-tie region, creating a lysing chamber.

Lysis of *Chlamydia trachomatis* Using Focused Microwave Irradiation.

*Chlamydia trachomatis* was exposed to microwave irradiation in the lysing chamber as described above. 500 pL of different diluted aliquots of the stock bacteria ($1.0 \times 10^7$ CFU·mL) were exposed to a 10 s microwave pulse. The CT solution after lysis was collected into vials for bacteria plate counting. The lysing volume and microwave power were precalibrated to 95° C. using 500 pL of buffer.

Bacteria Plate Counting.

Quantitation of *C. trachomatis* was performed from stocks of *chlamydia* organisms grown in McCoy cells by culturing 10-fold dilutions of the *chlamydia* in McCoy cell in tissue culture in triplicate. Titer in inclusion forming units/ml (IFU/ml) was determined by the average of the 3 countable wells for number of inclusions multiplied by the dilution factor and a factor of 10 as 100 ul was plated to achieve IFU/ml titer of the stock *chlamydia*. Aliquots of stock *chlamydia* organisms ($1.0 \times 10^7$ CFU/mL) were frozen for subsequent use in MAMEF experiments.

Figure 9:
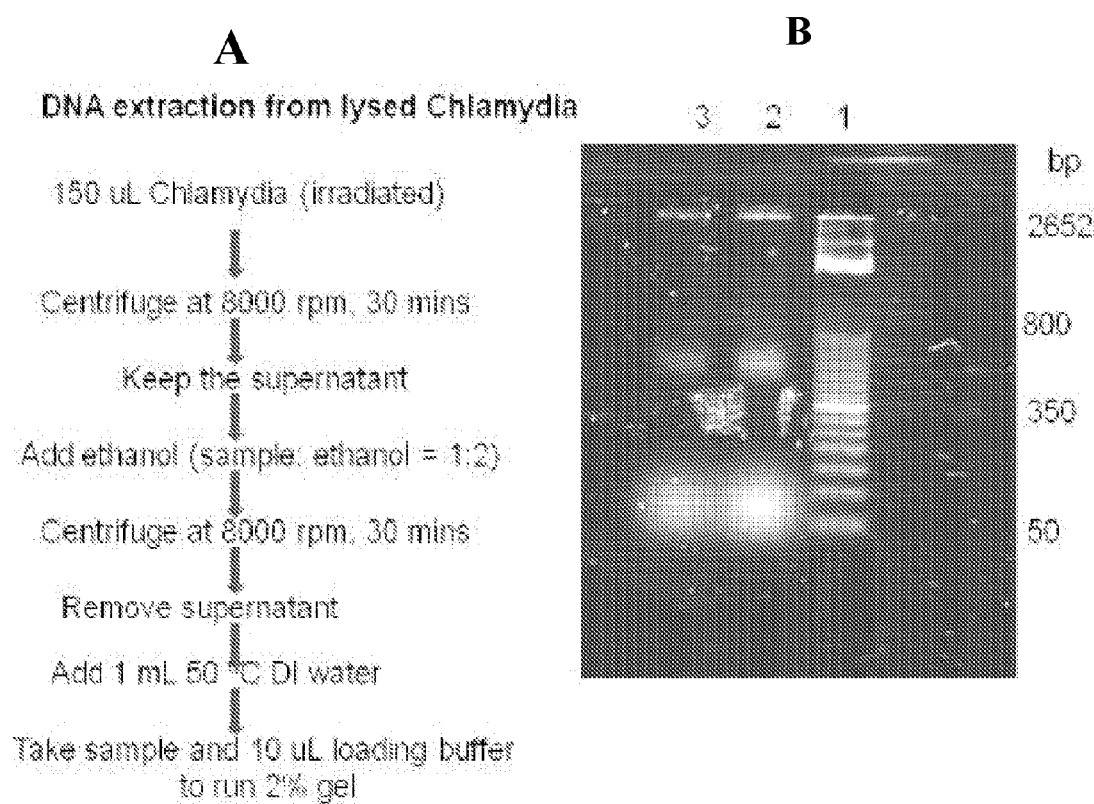
FIG. 9 A shows the flow diagram of DNA extraction from lysed *Chlamydia*. B) Ladders run on 2% agarose gel. Lane 1. E-gel 50 bp DNA markers ladder. Lane 2. 40 ul loading volume of lysed *Chlamydia* bacteria. Lane 3. 20 uL loading volume of lysed *Chlamydia* bacteria.
Figure 10:
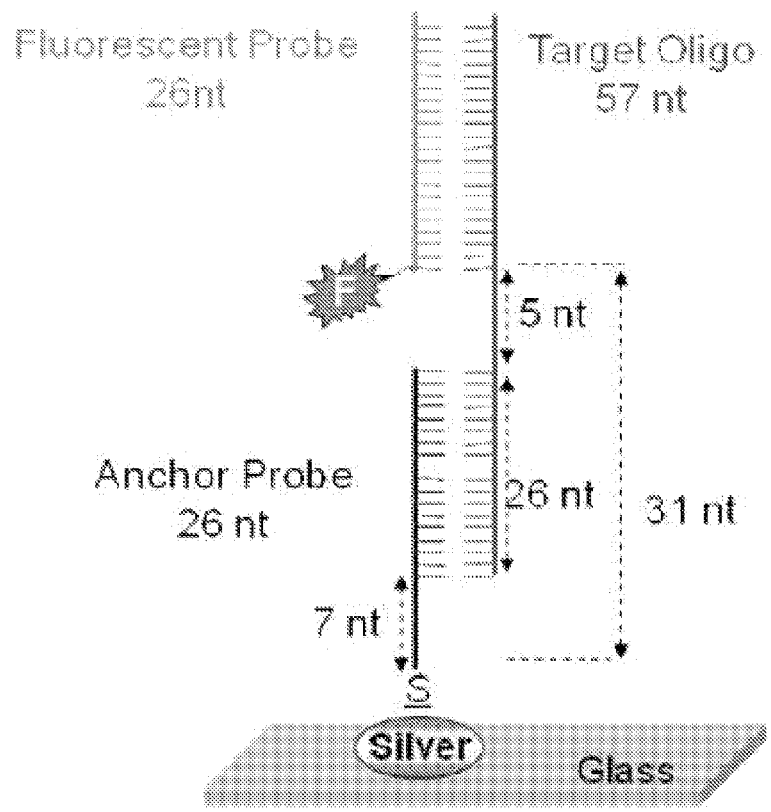
FIG. 10. (Top) MAMEF assay construction for *Chlamydia* DNA. The anchor (SEQ ID NO: 5) DNA probe, target (SEQ ID NO:7) DNA and fluorophore DNA probe (SEQ ID NO: 6), (Bottom).

Gel Electrophoresis. DNA was extracted from the lysed bacteria following the scheme shown in FIG. 9 left. 2% Agarose gels were prepared in 1×TAE buffer with Ethidium Bromide and run at 0.1 A on a power Pac electrophoresis device (Bio Rad Laboratories).

Design of Anchor and Fluorescent Probes.

The anchor (SEQ ID NO: 5) and fluorophore labeled DNA (SEQ ID NO: 6) probes were designed such that the anchor probe comprised 33 nucleotides and the terminal of the anchor probe was a thiol group, which readily binds to the silver surface. The fluorophore-labeled probe consisted of a region of 26 nucleotides homologous to the CT sequence. A TAMRA™ NHS Ester Dye was attached to the first nucleotide, to position it close to metal when the target CT (SEQ ID NO: 7) is present. This 3 pieced DNA construction has been described in detailed elsewhere[42]. The anchor probe and fluorophore labeled probe were purchased from IDT (Coralville, Iowa).

Formation of silver island films (SiFs) on glass substrates. The procedure has been described above.

Preparation of the MAMEF Assay Platform for the Ultra—Fast Detection of *Chlamydia trachomatis* DNA.

SiFs-deposited glass slides were coated with self adhesive silicon isolators, containing 2.0 mm diameter circular wells prior to the assay fabrication and subsequent fluorescence experiments. 100 μM of thiolated anchor probe was incubated overnight at 4° C. on the surface of SiFs-deposited glass slides in EDTA Buffer, (this buffer was used in all the experiments) followed by rinsing with water to remove the unbound material. The thiolated anchor probe was subsequently covalently linked to SiFs via well-established self-assembled monolayer chemistry[68].

MAMEF-Based *Chlamydia trachomatis* DNA Assays.

The MAMEF-based DNA capture assay was performed by the incubation of 15 pL lysed CT with varying different aliquots of stock CT solution mixed with 15 pL 1 nm TAMRA™-labeled fluorescent probe on the SIFs, for 30 seconds in a microwave cavity (a 0.7 cu ft, GE Compact Microwave Model: JES735BF, max power 700 W). The power setting of the microwave cavity was set to 2 which corresponded to 140 W over the entire cavity, a fraction of which is absorbed in our assay. This power is similar to the numerous reports using low power microwaves for immunolabeling, immunostaining, in immunocytochemistry and histological microwave processing. In all the experiments performed with low power microwaves using the SiFs surface, there was no evidence of sample drying. In the presence of the target CT DNA, the 3-piece assay is complete and enhanced fluorescence can be observed by the close proximity of the label to the silver substrate. Note: Enhanced fluorescence can only be seen in the presence of the CT target DNA.

Transmission Electron Microscopy.

TEMs were taken with a Electron Microscope Tecnai T12. Samples were drop cast onto Formvar carbon films on copper grids (400 mesh) by placing a droplet of a 10-pL aqueous sample solution onto the grid. The grid was dried in air for 24 h.

All fluorescence assay measurements were performed by collecting the emission intensity through a long pass filter (532 nm), using a 532 nm CW diode laser for excitation and a Fiber Optic Spectrometer (HD2000) from Ocean Optics, Inc., for the detection of the fluorescence emission.

Discussion

Lysis of CT Bacteria Using Gold Bow Ties and Focused Microwaves.

Figure 7:
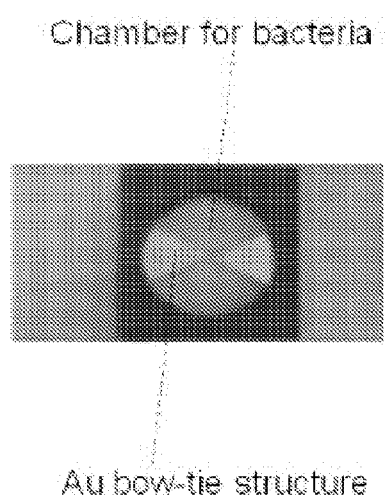
FIG. 7 shows (Left) A representative substrate of the experimental geometry used to release DNA from *Chlamydia*. Equilateral Gold triangles of 12.5 mm size (thickness 100 nm) are deposited onto a glass microscope slide. The gap between the two triangles is 1 mm and is covered with a 2 cm Diameter silicon well. (Right) 500 uL *Chlamydia* in different concentrations is microwave lysed inside the silicon well for 10 secs. The lysed rate and percentage of *Chlamydia* remaining was calculated after undertaking plate counting.

When exposed to 2.45-GHz microwave irradiation in a conventional microwave cavity, a significant and rapid heating at the gap (1 mm) of the 12.5 mm gold disjoined bow-tie geometries were observed (FIG. 7a). The disjoined bow-tie geometry was adopted to rapidly lyse *Chlamydia trachomatis*. In this regard, a small volume (150 pL) of bacteria ($1.0 \times 10^7$ cfu/mL) was placed in the gap of the gold triangles and was irradiated for 10 s in a microwave cavity. The subsequent lysate was incubated overnight and the living bacteria counted (FIG. 7). A 100% lysed rate (FIG. 7 Right) was observed, after the lysing chamber had been precalibrated not to boil over using a buffer solution.

Figure 11:
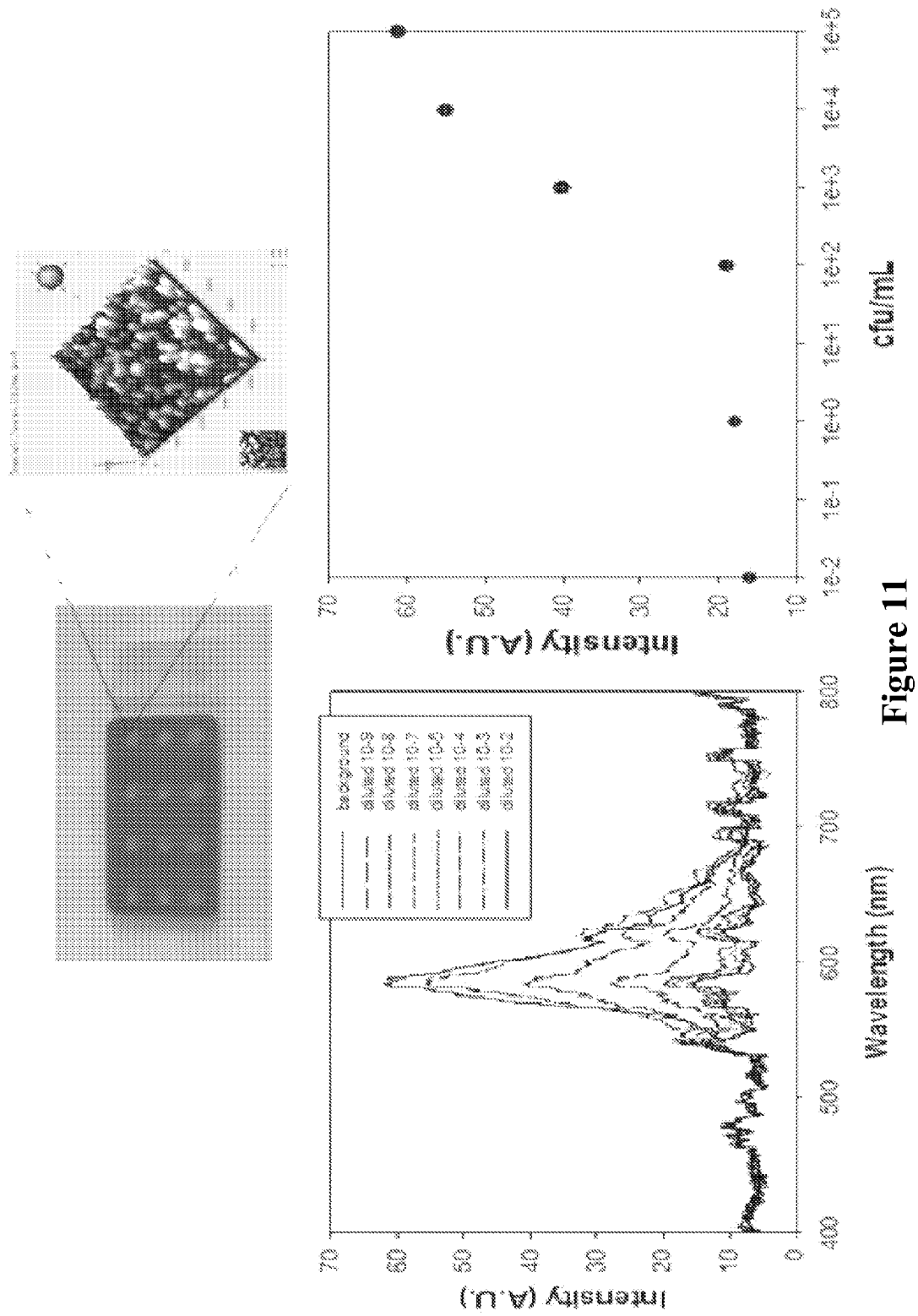
FIG. 11 (Top) AFM of SIFs as the substrate for the MAMEF assay. (Bottom) The fluorescence spectra of the fluorophore probe after incubation with target DNA. The intensity of the fluorophore probe is related to the varying concentration of *Chlamydia*.

Using TEM, the morphologies of the CT bacteria before and after lysis are shown in FIG. 8. *Chlamydia* are elongated ellipse-shaped ≈1000 nm in length. In the presence of the disjoined bow-tie antennas, no residual structure of CT was observed. The TEM images provided the visual evidence for the physical disruption of the bacteria and the potential release of DNA after focused microwave heating. To verify that DNA was in fact released from bacteria during irradiation, a quantitative evaluation of the release of DNA was undertaken using gel electrophoresis. From the gel results (FIG. 9 right) it can be seen that a significant amount of DNA released was mostly 50 and 600 base pairs (lane 2 and lane 3).

This exactly matched with the target CT DNA. These results confirmed that DNA was released from the CT in an analogous manner to how this technology was recently applied to the release of *Bacillus Anthracis* DNA from the spore form[42].

Microwave-Accelerated Detection of DNA Using the MAMEF Platform Technology.

The applicability of the MAMEF technology to a three piece DNA detection scheme (FIG. 10) whereby a silvered glass slide is modified with an anchor probe and a target DNA sequence is detected with a fluorescence probe in less than 30 s. In this scheme, the anchor probe and the fluorescent probe hybridize with different regions of the target DNA in proximity to the silver surface, where the fluorescent label is plasmon-enhanced, ultimately yielding an increased assay sensitivity. In the present invention, the MAMEF-based three-piece DNA detection scheme was adapted to detect DNA released from CT post lysing. By measuring the enhanced fluorescence spectra with varying concentrations of target DNA, a dilution curve was developed for the fluorescence intensity and concentration of lysed CT (FIG. 11). Using this approach, a detection limit of <100 cfu/mL CT has been achieved under 1 minute total time, which includes the sample preparation time.

\* \* \*

While the invention has been described herein with reference to specific features, aspects and embodiments, it will be recognized that the invention may be widely varied, and that numerous other variations, modifications and other embodiments will readily suggest themselves to those of ordinary skill in the art. Accordingly, the ensuing claims are to be broadly construed, as encompassing all such other variations, modifications and other embodiments, within their spirit and scope.

REFERENCES

All references discussed herein are hereby incorporated herein by reference for all purposes.
1. Levine, M. M. (1999) Typhoid Fever Vaccines. Plotkin, S. A and Orenstein, W. A. VaccinesThird, Philadelphia W.B. Saunders.
2. Adak G K, Long S M, O'Brien S J (2002) Trends in indigenous foodborne disease and deaths, England and Wales: 1992 to 2000. Gut 51: 832-841.
3. Voetsch A C, Van Gilder T J, Angulo F J, Farley M M, Shallow S, et al. (2004) FoodNet estimate of the burden of illness caused by nontyphoidal *Salmonella* infections in the United States. Clin Infect Dis 38 Suppl 3: S127-S134.
4. Vugia D J, Samuel M, Farley M M, Marcus R, Shiferaw B, et al. (2004) Invasive *Salmonella* infections in the United States, FoodNet, 1996-1999: incidence, serotype distribution, and outcome. Clin Infect Dis 38 Suppl 3: S149-S156.
5. Kennedy M, Villar R, Vugia D J, Rabatsky-Ehr T, Farley M M, et al. (2004) Hospitalizations and deaths due to *Salmonella* infections, FoodNet, 1996-1999. Clin Infect Dis 38 Suppl 3: S142-S148.
6. Berkley J A, Lowe B S, Mwangi I, Williams T, Bauni E, et al. (2005) Bacteremia among children admitted to a rural hospital in Kenya. N Engl J Med 352: 39-47.
7. Graham S M, Molyneux E M, Walsh A L, Cheesbrough J S, Molyneux M E, et al. (2000) Nontyphoidal *Salmonella* infections of children in tropical Africa. Pediatr Infect Dis J 19: 1189-1196.
8. Hill P C, Onyeama C O, Ikumapayi U N, Secka O, Ameyaw S, et al. (2007) Bacteraemia in patients admitted to an urban hospital in West Africa. BMC Infect Dis 7: 2.
9. Ikumapayi U N, Antonio M, Sonne-Hansen J, Biney E, Enwere G, et al. (2007) Molecular epidemiology of community-acquired invasive non-typhoidal *Salmonella* among children aged 2-29 months in rural Gambia and discovery of a new serovar, *Salmonella enterica* Dingiri. J Med Microbiol 56: 1479-1484.
10. Kariuki S, Revathi G, Kariuki N, Kiiru J, Mwituria J, et al. (2006) Characterisation of community acquired non-typhoidal *Salmonella* from bacteraemia and diarrhoeal infections in children admitted to hospital in Nairobi, Kenya. BMC Microbiol 6: 101.
11. Levy H, Diallo S, Tennant S M, Livio S, Sow S O, et al. (2008) PCR method to identify *Salmonella enterica* serovars *Typhi, Paratyphi* A, and *Paratyphi* B among *Salmonella* isolates from the blood of patients with clinical enteric fever. J Clin Microbiol 46: 1861-1866.
12. Walsh A L, Phiri A J, Graham S M, Molyneux E M, Molyneux M E (2000) Bacteremia in febrile Malawian children: clinical and microbiologic features. Pediatr Infect Dis J 19: 312-318.
13. Jones T F, Ingram L A, Cieslak P R, Vugia D J, Tobin-D'Angelo M, et al. (2008) Salmonellosis outcomes differ substantially by serotype. J Infect Dis 198: 109-114.
14. Gradel K O, Schonheyder H C, Pedersen L, Thomsen R W, Norgaard M, et al. (2006) Incidence and prognosis of non-typhoid *Salmonella* bacteraemia in Denmark: a 10-year county-based follow-up study. Eur J Clin Microbiol Infect Dis 25: 151-158.
15. Papaevangelou V, Syriopoulou V, Charissiadou A, Pangalis A, Mostrou G, et al. (2004) *Salmonella* bacteraemia in a tertiary children's hospital. Scand J Infect Dis 36: 547-551.
16. Threlfall E J, Hall M L, Rowe B (1992) *Salmonella* bacteraemia in England and Wales, 1981-1990. J Clin Pathol 45: 34-36.
17. Brent A J, Oundo J O, Mwangi I, Ochola L, Lowe B, et al. (2006) *Salmonella* bacteremia in Kenyan children. Pediatr Infect Dis J 25: 230-236.
18. Graham S M, Walsh A L, Molyneux E M, Phiri A J, Molyneux M E (2000) Clinical presentation of non-typhoidal *Salmonella* bacteraemia in Malawian children. Trans R Soc Trop Med Hyg 94: 310-314.
19. Lepage P, Bogaerts J, Van Goethem C, Ntahorutaba M, Nsengumuremyi F, et al. (1987) Community-acquired bacteraemia in African children. Lancet 1: 1458-1461.
20. Mandomando I, Macete E, Sigauque B, Morais L, Quinto L, et al. (2009) Invasive non-typhoidal *Salmonella* in Mozambican children. Trop Med Int Health 14: 1467-1474.
21. O'Dempsey T J, McArdle T F, Lloyd-Evans N, Baldeh I, Laurence B E, et al. (1994) Importance of enteric bacteria as a cause of pneumonia, meningitis and septicemia among children in a rural community in The Gambia, West Africa. Pediatr Infect Dis J 13: 122-128.
22. Reisner B S, Woods G L (1999) Times to detection of bacteria and yeasts in BACTEC 9240 blood culture bottles. J Clin Microbiol 37: 2024-2026.
23. Durmaz G, Us T, Aydinli A, Kiremitci A, Kiraz N, et al. (2003) Optimum detection times for bacteria and yeast species with the BACTEC 9120 aerobic blood culture system: evaluation for a 5-year period in a Turkish university hospital. J Clin Microbiol 41: 819-821.
24. Wain J, Hosoglu S (2008) The laboratory diagnosis of enteric fever. J Infect Developing Countries 2: 421-425.
25. Malorny B, Lofstrom C, Wagner M, Kramer N, Hoorfar J (2008) Enumeration of *Salmonella* bacteria in food and feed samples by real-time PCR for quantitative microbial risk assessment. Appl Environ Microbiol 74: 1299-1304.
26. Malorny B, Huehn S, Dieckmann R, Kramer N, Helmuth R (2008) Polymerase chain reaction for the rapid detection and serovar identification of *Salmonella* in food and feeding stuff. Food Anal Methods.
27. Ali A, Haque A, Haque A, Sarwar Y, Mohsin M, et al. (2009) Multiplex PCR for differential diagnosis of emerging typhoidal pathogens directly from blood samples. Epidemiol Infect 137: 102-107.
28. Frankel G (1994) Detection of *Salmonella typhi* by PCR. J Clin Microbiol 32: 1415.
29. Haque A, Ahmed N, Peerzada A, Raza A, Bashir S, et al. (2001) Utility of PCR in diagnosis of problematic cases of typhoid. Jpn J Infect Dis 54: 237-239.
30. Hatta M, Smits H L (2007) Detection of *Salmonella typhi* by nested polymerase chain reaction in blood, urine, and stool samples. Am J Trop Med Hyg 76: 139-143.
31. Kumar A, Arora V, Bashamboo A, Ali S (2002) Detection of *Salmonella typhi* by polymerase chain reaction: implications in diagnosis of typhoid fever. Infect Genet Evol 2: 107-110.
32. Massi M N, Shirakawa T, Gotoh A, Bishnu A, Hatta M, et al. (2003) Rapid diagnosis of typhoid fever by PCR assay using one pair of primers from flagellin gene of *Salmonella typhi*. J Infect Chemother 9: 233-237.
33. Prakash P, Mishra O P, Singh A K, Gulati A K, Nath G (2005) Evaluation of nested PCR in diagnosis of typhoid fever. J Clin Microbiol 43: 431-432.
34. Sanchez-Jimenez M M, Cardona-Castro N (2004) Validation of a PCR for diagnosis of typhoid fever and salmonellosis by amplification of the hilA gene in clinical samples from Colombian patients. J Med Microbiol 53: 875-878.
35. Song J H, Cho H, Park M Y, Na D S, Moon H B (1993) Detection of *Salmonella typhi* in the blood of patients with typhoid fever by polymerase chain reaction. J Clin Microbiol 31: 1439-1443.
36. Wain J, Pham V B, Ha V, Nguyen N M, To S D, et al. (2001) Quantitation of bacteria in bone marrow from patients with typhoid fever: relationship between counts and clinical features. J Clin Microbiol 39: 1571-1576.
37. Wain J, Diep T S, Ho V A, Walsh A M, Nguyen T T, et al. (1998) Quantitation of bacteria in blood of typhoid fever patients and relationship between counts and clinical features, transmissibility, and antibiotic resistance. J Clin Microbiol 36: 1683-1687.
38. Watson K C (1955) Isolation of *Salmonella typhi* from the blood stream. J Lab Clin Med 46: 128-134.
39. Aslan K, Geddes C D (2008) New tools for rapid clinical and bioagent diagnostics: microwaves and plasmonic nanostructures. Analyst 133: 1469-1480.
40. Aslan K, Geddes C D (2008) A review of an ultrafast and sensitive bioassay platform technology: Microwave-accelerated metal-enhanced fluorescence. Plasmonics 3: 89-101.
41. Aslan K, Zhang Y, Hibbs S, Baillie L, Previte M J, et al. (2007) Microwave-accelerated metal-enhanced fluorescence: application to detection of genomic and exosporium anthrax DNA in <30 seconds. Analyst 132: 1130-1138.
42. Aslan K, Previte M J, Zhang Y, Gallagher T, Baillie L, et al. (2008) Extraction and detection of DNA from *Bacillus anthracis* spores and the vegetative cells within 1 min. Anal Chem 80: 4125-4132.
43. Zhang Y, Agreda P, Kelley S, Gaydos C, Geddes C D (2010) Development of a Microwave—Accelerated Metal-Enhanced Fluorescence 40 second, 100 cfu/mL Point of Care Assay for the Detection of *Chlamydia trachomatis*. IEEE Trans Biomed Eng.
44. Aslan K, Holley P, Geddes C D (2006) Microwave-Accelerated Metal-Enhanced Fluorescence (MAMEF) with silver colloids in 96-well plates: Application to ultra fast and sensitive immunoassays, High Throughput Screening and drug discovery. J Immunol Methods 312: 137-147.
45. Aslan K, Leonenko Z, Lakowicz J R, Geddes C D (2005) Annealed silver-island films for applications in metal-enhanced fluorescence: interpretation in terms of radiating plasmons. J Fluoresc 15: 643-654.
46. Tennant S M, Diallo S, Levy H, Livio S, Sow S O, et al. (2010) Identification by PCR of non-typhoidal *Salmonella enterica* serovars associated with invasive infections among febrile patients in Mali. PLoS Negl Trop Dis 4: e621.
47. Nga T V, Karkey A, Dongol S, Thuy H N, Dunstan S, et al. (2010) The sensitivity of real-time PCR amplification targeting invasive *Salmonella* serovars in biological specimens. BMC Infect Dis 10: 125.
48. Zhou L, Pollard A J (2010) A fast and highly sensitive blood culture PCR method for clinical detection of *Salmonella enterica* serovar *Typhi*. Ann Clin Microbiol Antimicrob 9: 14.
49. Almeida C, Azevedo N F, Fernandes R M, Keevil C W, Vieira M J (2010) Fluorescence in situ hybridization method using a peptide nucleic acid probe for identification of *Salmonella* spp. in a broad spectrum of samples. Appl Environ Microbiol 76: 4476-4485.
50. Lehmann L E, Hunfeld K P, Emrich T, Haberhausen G, Wissing H, et al. (2008) A multiplex real-time PCR assay for rapid detection and differentiation of 25 bacterial and fungal pathogens from whole blood samples. Med Microbiol Immunol 197: 313-324.
51. Mancini N, Clerici D, Diotti R, Perotti M, Ghidoli N, et al. (2008) Molecular diagnosis of sepsis in neutropenic patients with haematological malignancies. J Med Microbiol 57: 601-604.
52. Paolucci M, Capretti M G, Dal M P, Corvaglia L, Landini M P, et al. (2009) Laboratory diagnosis of late-onset sepsis in newborns by multiplex real-time PCR. J Med Microbiol 58: 533-534.
53. Aslan K (2010) Rapid Whole Blood Bioassays using Microwave-Accelerated Metal-Enhanced Fluorescence. Nano Biomed Eng 2: 1-9.
54. Woods D F, Reen F J, Gilroy D, Buckley J, Frye J G, et al. (2008) Rapid multiplex PCR and real-time TaqMan PCR assays for detection of *Salmonella enterica* and the highly virulent serovars *Choleraesuis* and *Paratyphi* C. J Clin Microbiol 46: 4018-4022.
55. Widjojoatmodjo M N, Fluit A C, Torensma R, Keller B H, Verhoef J (1991) Evaluation of the magnetic immuno PCR assay for rapid detection of *Salmonella*. Eur J Clin Microbiol Infect Dis 10: 935-938.
56. Centers for Disease Control and Prevention, sexually transmitted disease surveillance, 2008. Atlanta, Ga.: U.S. Department of Health and Human Services, CDC., 2010.
57. E. T, 'The Hidden Epidemic: Confronting Sexually Transmitted Diseases. Washington. D.C.: National Academy Press. 1997.
58. "APHL/CDC Panel Summary Reports, Laboratory Diagnostic Testing for *Chlamydia trachomatis* and *Neisseria gonorrhoeae*, and Laboratory Diagnostic Testing for *Treponema pallidum*. 2009. Guidelines for the Laboratory Testing of STDs. http://www.aphl.org/aphlprograms/infectious/std/Pages/stdtestingguidelines.aspx.'"
59. C. A. Gaydos, C. QuinnT, D. Willis, A. Weissfeld, E. W. Hook, D. H. Martin, D. V. Ferrero, and J. Schachter, 'Performance of the APTIMA Combo 2 assay for the multiplex detection of *Chlamydia trachomatis* and *Neis-* seria gonorrheae in female urine and endocervical swab specimens.,' J Clin Microbiol vol. 304, pp. 304-309, 2003.
60. Van Der Pol, D. F. B., L. Buck-Barrington, E. Hook III, C. Lenderman, T. C. Quinn, C. A. Gaydos, J. Moncada, G. Hall, M. J. Tuohy, and B. R. Jones., 'Multicenter evaluation of the BDProbeTec ET system for the detection of Chalmydia trachomatis and *Neisseria gonorrhoeae* in urine specimens, female endocervical swabs, and male urethral swabs.' J Clin Microbiol, vol. 39, pp. 1008-1016, 2001.
61. B. Van Der Pol, T. C. Quinn., G. C. A., K. Crotchfelt, J. Schachter, J. Moncada, D. Jungkind, D. H. Martin, B. Turner, C. Peyton, and R. B. Jones., 'Evaluation of the AMPLICOR and Automated COBAS AMPLICOR CT/NG Tests for the Detection of *Chlamydia trachomatis*,' J Clin Microbiol vol. 38, pp. 1105-1112., 2000.
62. J. Huppert, E. Hesse, C. A. Gaydos, and 'What's the point? How point-of-care sexually transmitted infection tests can impact infected patients.,' Point of Care, vol. 9, pp. 36-46, 2010.
63. K. Aslan, S, N. Malyn, G. Bector, and C. D. Geddes, 'Microwave-accelerated metal-enhanced fluorescence: an ultra-fast and sensitive DNA sensing platform,' Analyst, vol. 132, pp. 1122-9, November 2007.
64. K. Aslan, Y. Zhang, S. Hibbs, L. Baillie, M. J. Previte, and C. D. Geddes, 'Microwave-accelerated metal-enhanced fluorescence: application to detection of genomic and exosporium anthrax DNA in <30 seconds,' Analyst, vol. 132, pp. 1130-8, November 2007.
65. K. Aslan and C. D. Geddes, 'Microwave-accelerated Metal-enhanced Fluorescence (MAMEF): Application to ultra fast and sensitive clinical assays,' Journal of Fluorescence, vol. 16, pp. 3-8, 2006.
66. C. D. Geddes, 'Metal-enhanced fluorescence II: Progress towards a unified plasmon-fluorophore description,' Journal of fluorescence, vol. in press, 2009.
67. R. Pribik, A. I. Dragan, Y. Zhang, C. Gaydos, and C. D. Geddes, 'Metal-Enhanced Fluorescence (MEF): Physical characterization of silver Island Films and exploring sample geometries,' Chemical Physics Letters, vol. 478, pp. 70-74, 2009.
68. M. T. Owain P. H. Vaughan, Federico J. Williams, Andreas Hille, Jeremy K. M. Sanders, and Richard M. Lamber, 'Direct Observation of Surface-Mediated Thioacetyl Deprotection: Covalent Tethering of a Thiol-Terminated Porphyrin to the Ag(100) Surface,' J. Am. Chem. Soc., vol. 128, pp. 9578-9579, 2006.
69. K. Aslan, P. Holley, and C. D. Geddes, 'Microwave-Accelerated Metal-Enhanced Fluorescence (MAMEF) with silver colloids in 96-well plates: Application to ultra fast and sensitive immunoassays, High Throughput Screening and drug discovery,' Journal of Immunological Methods, vol. 312, pp. 137-147, 2006.
70. K. Aslan and C. D. Geddes, 'Microwave-accelerated metal-enhanced fluorescence: Platform technology for ultrafast and ultrabright assays,' Analytical Chemistry, vol. 77, pp. 8057-8067, 2005.
71. K. Aslan and C. D. Geddes, 'Microwave Accelerated and Metal Enhanced Fluorescence Myoglobin Detection on Silvered Surfaces: Potential Application to Myocardial Infarction Diagnosis,' Plasmonics, vol. 1, pp. 53-59, 2006.

That which is claimed is:

1. A method for detecting a pathogenic microorganism in a sample, the method comprising:
 a) providing a system comprising:
  i) a first surface substrate comprising immobilized triangular metallic structures, wherein the metallic structures are in a patterned shape of a bow-tie wherein the apexes of two triangles are arranged in alignment and forming a reactive zone between the apexes;
  ii) a second surface substrate comprising immobilized metallic islands or colloids, wherein the metallic islands or colloids has attached thereto an immobilized capture DNA sequence probe complementary to a known DNA sequence of the pathogenic microorganism;
  iii) a free capture DNA sequence probe complementary to a known DNA sequence of the pathogenic microorganism, wherein the free capture DNA sequence probe has attached thereto an excitable light emitting molecule;

iv) a source of electromagnetic energy for providing energy in the microwave energy range and to excite the excitable light emitting molecule; and
v) a measuring device to measure electromagnetic emissions;
b) contacting the sample with the first surface substrate and positioning the pathogenic microorganism in the reactive zone;
c) exposing the reactive zone to microwave energy in an amount sufficient to lyse cellular membranes of the pathogenic microorganism to form a lysed pathogenic microorganism;
d) removing the lysed pathogenic microorganism from the first substrate and isolating the DNA from the lysed pathogenic microorganism;
e) contacting the isolated DNA with the immobilized capture DNA sequence probe on the second substrate, wherein the isolated DNA binds to the immobilized capture DNA sequence probe;
f) introducing the free capture DNA sequence probe for contact with any bound DNA of pathogenic microorganism, wherein binding of the free capture DNA sequence probe to the DNA of pathogenic microorganism causes the excitable light emitting molecule to be positioned a sufficient distance from the immobilized metallic islands or colloids to enhance emission levels when excited by an irradiating source;
g) exposing the binding reactions of steps (e) and (f) to microwave energy in an amount sufficient to increase the reaction rate; and
g) identifying the pathogenic microorganism by luminescence emission by irradiating the system with the electromagnetic energy source to excite the excitable light emitting molecule.

2. The method of claim 1, wherein the light emitting molecule is selected from the group consisting of fluorophores, luminophores, bioluminescent species and chemiluminescent species.

3. The method of claim 1, wherein the triangular shaped metallic structure is fabricated from a metallic material selected from the group consisting of silver, gold, copper, zinc, indium, rhodium, aluminum, and platinum.

4. The method of claim 3, wherein the metallic material is gold.

5. The method of claim 1, wherein the reactive zone has a diameter from about 0.01 mm to 5 mm.

6. The method of claim 5, wherein the diameter is from about 1 mm to 3 mm.

7. The method of claim 6, wherein the reactive zone is within a well of an assay system.

8. The method of claim 1, wherein the pathogen causes smallpox, tularemia, botulism, anthrax, *Chlamydia*, or *salmonella*.

9. The method of claim 1, wherein the pathogen is one wherein the DNA sequence is known or easily determined.

10. The method of claim 1, wherein the first and second substrate is fabricated from a polymeric material, glass, paper, nitrocellulose or combinations thereof.

11. The method of claim 1, wherein the light emitting molecule is positioned from about 5 nm to about 200 nm from the immobilized metallic structures to enhance light and/or electromagnetic emission.

12. The method of claim 1, wherein the light emitting molecule is positioned from about 5nm to about 40 nm from the immobilized metallic structures to enhance light and/or electromagnetic emission.

13. The method of claim 1, wherein the microwave energy in an amount sufficient to lyse cellular membranes of the pathogenic microorganism has a power level in a range from 300 watts to 1000 watts.

14. The method of claim 1, wherein the pathogenic microorganism is a bacterium, virus, yeast or algae.

15. An assay system for determining a target pathogen comprising:
a surface substrate comprising immobilized triangular shaped metallic structures positioned in a patterned shape of a bow-tie wherein apexes of two triangular shaped metallic structures are arranged in alignment and forming a reactive zone between the apexes;
a captured DNA probe complementary to a known DNA sequence of the target pathogen immobilized on the triangular shaped metallic structures;
a free DNA probe complementary to the known DNA of the target pathogen, wherein the free DNA probe has attached thereto an excitable light emitting molecule, wherein binding of the immobilized and free DNA probe to the known DNA sequence of the target pathogen causes the excitable light emitting molecule to be positioned from about 5 nm to about 200 nm from the immobilized triangular shaped metallic structures to enhance light and/or electromagnetic emission.

* * * * *

SEQUENCE LISTING

<160> NUMBER OF SEQ ID NOS: 7

<210> SEQ ID NO 1
<211> LENGTH: 22
<212> TYPE: DNA
<213> ORGANISM: Artificial Sequence
<220> FEATURE:
<223> OTHER INFORMATION: Synthetic construct

<400> SEQUENCE: 1
gtttttcaac ctgttttgcg cc                                              22

<210> SEQ ID NO 2
<211> LENGTH: 19
<212> TYPE: DNA
<213> ORGANISM: Artificial Sequence
<220> FEATURE:
<223> OTHER INFORMATION: Synthetic Construct

<400> SEQUENCE: 2
ctttcagttc cgcttctat                                                  19

<210> SEQ ID NO 3
<211> LENGTH: 39
<212> TYPE: DNA
<213> ORGANISM: Artificial Sequence
<220> FEATURE:
<223> OTHER INFORMATION: Synthetic construct

<400> SEQUENCE: 3
atagaagcgg aactgaaagg cgctggcgca aaacaggtg                            39

```
<210> SEQ ID NO 4
<211> LENGTH: 554
<212> TYPE: DNA
<213> ORGANISM: Artificial Sequence
<220> FEATURE:
<223> OTHER INFORMATION: Synthetic Construct

<400> SEQUENCE: 4
ggatcctgat aaaacatggt aattgcctcg cataacgcgg tgtgaaaatg gattgaagcc     60
cgggcggtgg attctactca actttagccg atggagaaag ccccgggatc cgggctatta    120
aaaagaagat cttttattt agagatctgt tctattgtga tctcttatta ggatcgcgcc     180
aggctgtgga tacccggat cctgtaataa agatcaatgc gttggaaagg atcactagct     240
gtgaatgatc ggtgatcgtg gtccgtataa gctgggatca aaacgggtac ttatacacaa    300
ctcaaaaagt gaacaacggt tattctttgg ataactaccg gttgatccaa gctttccacc    360
agatttatcc acaatggatc gcacgatctt tacacttatt tgagtaaatt aatccaggat    420
ccgagccaaa tctccgctgg atcttccgga atctcatgtt caaggatgtt gatcttcagt    480
gtttccccaa cctgttttgc gccagcgcct ttcagttccg cttctatttt ctcaatcgcg    540
ccgcaaaacg tgtc                                                      554

<210> SEQ ID NO 5
<211> LENGTH: 33
<212> TYPE: DNA
<213> ORGANISM: Artificial Sequence
<220> FEATURE:
<223> OTHER INFORMATION: Synthetic Construct

<400> SEQUENCE: 5 ctttttggc gatatttggg catccgagta acg                                   33

<210> SEQ ID NO 6
<211> LENGTH: 26
<212> TYPE: DNA
<213> ORGANISM: Artificial Sequence
<220> FEATURE:
<223> OTHER INFORMATION: Synthetic construct

<400> SEQUENCE: 6 gaagggatc ttaggaccttt tcggtt                                          26

<210> SEQ ID NO 7
<211> LENGTH: 76
<212> TYPE: DNA
<213> ORGANISM: Artificial Sequence
<220> FEATURE:
<223> OTHER INFORMATION: Synthetic construct

<400> SEQUENCE: 7
tatggcttac accgctataa acccgtaggc tcattgcaat ttcttcccct agaatcctgg     60
aaagccaatt ccctct                                                    76
```